US007001742B1

(12) United States Patent
Liu et al.

(10) Patent No.: US 7,001,742 B1
(45) Date of Patent: Feb. 21, 2006

(54) HUMAN UNCOUPLING PROTEIN 3

(75) Inventors: Qingyun Liu, North Wales, PA (US); Fang Chen, North Wales, PA (US)

(73) Assignee: Merck & Co., Inc., Rahway, NJ (US)

( * ) Notice: Subject to any disclaimer, the term of this patent is extended or adjusted under 35 U.S.C. 154(b) by 17 days.

(21) Appl. No.: 09/081,737

(22) Filed: May 19, 1998

Related U.S. Application Data

(60) Provisional application No. 60/069,141, filed on Dec. 9, 1997, provisional application No. 60/047,179, filed on May 20, 1997.

(51) Int. Cl.
   *C12P 21/06* (2006.01)
   *C07H 17/00* (2006.01)
   *C07K 14/00* (2006.01)

(52) U.S. Cl. .................. 435/69.1; 536/23.1; 435/320.1; 435/252.1; 435/325; 530/350

(58) Field of Classification Search ................ 435/69.1, 435/320.1, 325, 252.1; 536/23.1, 23.5
   See application file for complete search history.

(56) References Cited

FOREIGN PATENT DOCUMENTS

| WO | WO 98/39432 | 9/1998 |
|---|---|---|
| WO | WO 98/50542 | 11/1998 |

OTHER PUBLICATIONS

Boss, O. et al.; Uncoupling protein-3: a new member of the mitochondrial carrier family with tissue-specific expression; FEBS Letters 408; (1997); pp 39-42.
Bouillaud et al.; Complete cDNA-derived Amino Acid Sequence of Rat Brown Fat Uncoupling Proten; J. Biol. Chem.; vol. 261; No. 4; (1986); pp1487-1490.
Bouillaud et al.; The Gene for Rat Uncoupling Protein: Complete Sequence, Structure of Primary Transcript and Evolutionary Relationship Between Exons; Biochem. Biophys Res. Comm.; vol. 157; No. 2; (1988); pp 783-792.
Nicholls, D. G. et al.; Thermogenic Mechanisms in Brown Fat; Physiological Reviews; vol. 64; No. 1; (1984); pp 1-64.
Jacobsson, A. et al.; Mitochondrial Uncoupling Protein from Mouse Brown Fat; J. Biological Chem; vol. 260; No. 30; (1985); pp 16250-16254.
Kozak, L. P. et al.; The Mitochondrial Uncoupling Protein Gene; J. Biological Chem; vol. 263; No. 25; (1988); pp 12274-12277.

Cassard, A-M. et al.; Human Uncoupling Protein Gene: Structure, Comparison with Rat Gene, and Assignment to the Long Arm of Chromosome 4; J. Cellular Biochemistry; vol. 43; (1990); pp 255-264.
Fleury, C. et al.; Uncoupling protein-2: a novel gene linked to obesity and hyperinsulinemia; Nature Genetics; vol. 15; (1997); pp 269-272.
Gimeno, R. E. et al.; Cloning and Characterization of an Uncoupling Protein Homolog: Diabetes; vol. 46; (1997); pp 900-906.
Taylor, B. A. et al.; Detection of Obesity QTLs on Mouse Chromosomes 1 and 7 by Selective DNA Pooling: Genomics; vol. 34; (1996); pp 389-398.
Bouillaud, F. et al.; A sequence related to a DNA recognition element is essential for the inhibition by nucleotides of proton transport through the mitochondrial uncoupling protein; The EMBO J.; vol. 13; No. 8: (1994); pp 1990-1997.
Gonzalez-Barroso, M.M. et al.; Activation of the uncoupling protein by fatty acides is modulated by mutations in the C-terminal region of the protein; Eur. J. Biochem; vol. 239; (1996); pp 445-450.
Frohman, M. A. et al.; Rapid production of full-length cDNAs from rare transcripts: Amplification using a single gene-specific oligonucleotide primer; Proc. Natl. Acad. Sci. USA; vol. 85; (1988); pp 8998-9002.
Matsuda et al. "Cloning of rat uncoupling protein-3 and uncoupling protein-2 cDNAs: their gene expression in rats fed high-fat diet" in FEBS Letters, vol. 418, pp. 200-204 (1997).
Yoshitomi et al., "Cloning of mouse uncoupling protein 3 cDNA and 5'-flanking region, and its genetic map", Gene, vol. 215, pp. 77-84 (1998).

*Primary Examiner*—Karen Cochrane Carlson
(74) *Attorney, Agent, or Firm*—Yang Xu; Jack Tribble

(57) ABSTRACT

An isolated nucleic acid molecule is disclosed which encodes a novel human uncoupling protein (UCP3), and related recombinant expression vectors, recombinant host cells and substantially purified forms of the UCP3 protein. The isolated nucleic acid and proteins disclosed herein will be useful in methods associated with identifying compounds which modulate energy expenditure and body weight regulation, as well as effecting diseases such as obesity and diabetes as well as mitochondria-associated hypermetabolism. Additionally, the isolated nucleic acids of the present invention are candidates for gene therapy of a mammalian host, including humans.

13 Claims, 16 Drawing Sheets

```
   1 TCGAACTCAC TCACCTCCCC TCTCACCTCA CTGCCCTCAC CAGCCAGCCT
  51 CTTGTCAAGT GATCAGGCTG TCAACCAACT TCTCTAGGAT AAGGTTTCAG
 101 GTCAGCCTGT GTGTATAAGA CCAGTGCCAA GCCAGAAGCA GCAGAGACAA
 151 CAGTGAATGA CAAGGAGGGG CCATCCAATC CCTGCTGCCA CCTCCTGGGA
 201 TGGAGCCCTA GGGAGCCCCT GTGCTGCCCC TGCCGTGGCA GGACTCACAG
 251 CCCCACCGCT GCACTGAAGC CCAGGGCTGT GGAGCAGCTC TCTCCTTGGA
 301 CTCCTCTCGG CCCTAAAGGG ACTGGGCAGA GCCTTCCAGG ACTATGGTTG
 351 GACTGAAGCC TTCAGACGTG CCTCCCACCA TGGCTGTGAA GTTCCTGGGG
 401 GCAGGCACAG CAGCCTGTTT TGCTGACCTC GTTACCTTTC CACTGGACAC
 451 AGCCAAGGTC CGCCTGCAGA TCCAGGGGGA GAACCAGGCG GTCCAGACGG
 501 CCCGGCTCGT GCAGTACCGT GGCGTGCTGG GCACCATCCT GACCATGGTG
 551 CGGACTGAGG GTCCCTGCAG CCCCTACAAT GGGCTGGTGG CCGGCCTGCA
 601 GCGCCAGATG AGCTTCGCCT CCATCCGCAT CGGCCTTTAC GACTCCGTCA
 651 AGCAGGTGTA CACCCCCAAA GGCGCGGACA ACTCCAGCCT CACTACCCGG
 701 ATTTTGGCCG GCTGCACCAC AGGAGCCATG GCGGTGACCT GTGCCCAGCC
 751 CACAGATGTG GTGAAGGTCC GATTTCAGGC CAGCATACAC CTCGGGCCAT
 801 CCAGGAGCGA CAGAAAATAC AGCGGGACTA TGGACGCCTA CAGAACCATC
 851 GCCAGGGAGG AAGGAGTCAG GGGCCTGTGG AAAGGAACTT TGCCCAACAT
 901 CATGAGGAAT GCTATCGTCA ACTGTGCTGA GGTGGTGACC TACGACATCC
 951 TCAAGGAGAA GCTGCTGGAC TATCACCTGC TCACTGACAA CTTCCCCTGC
1001 CACTTTGTCT CTGCCTTTGG AGCCGGCTTC TGTGCCACAG TGGTGGCCTC
1051 CCCGGTGGAC GTGGTGAAGA CCCGGTATAT GAACTCACCT CCAGGCCAGT
1101 ACTTCAGCCC CCTCGACTGT ATGATAAAGA TGGTGGCCCA GGAGGGCCCC
1151 ACAGCCTTCT ACAAGGGATT TACACCCTCC TTTTTGCGTT TGGGATCCTG
1201 GAACGTGGTG ATGTTCGTAA CCTATGAGCA GCTGAAACGG GCCCTGATGA
1251 AAGTCCAGAT GTTACGGGAA TCACCGTTTT GAACAAGACA AGAAGGCCAC
1301 TGGTAGCTAA CGTGTCCGAA ACCAGTTAAG AATGGAAGAA AACGGTGCAT
```

FIG. 1A

1351 CCACGCACAC ATGGACACAG ACCCACACAT GTTTACAGAA CTGTTGTTTA

1401 CTTGTTGCTG ATTCAAGAAA CAGAAGTAGA AGAGAGAGGA TTCTGGTCTT

1451 CACTGCCATG CCTCAAGAAC ACCTTTGTTT TGCACTGACA AGATGGAAAA

1501 TAAATTATAT TAATTTTTGA AACCCATTAG GCATGCCTAA TATTTAGGCA

1551 AGAGAAAATA AACCAAGATA GATCCATTTG GACAAAATGG AAGGTTGGAG

1601 ACGTGTATCC CCGTGAAATC TGGTCAGATA ATGAATGATA AGCAGGAAGG

1651 ATGGCAAGCA CGGGACAGGA GGGGCCCACA ATGGAGTGGG AGATCAGCCA

1701 CGGAGCCTGG AGGGACGCCA CCCAGCAACA CAGAGCTGGC GACTGCAGCT

1751 GCACCATCAC ACATGCATCA TCAGCCTATT TGTAATATGT CTGCCACAGA

1801 GAGTCCTTTG GGATTCTAGG AAACCCAAGG AACAAGAGAA AAAACTAGAG

1851 CCTGTGCTAA AGAAGCCTGC TGGGCCCATG TGAGGCTGGG GTCGTAAATA

1901 TTCCCCGACG ACACTGAAGA ATCAAGAGGG CAGCCCCCAC TTCTCCTACA

1951 AAATGGAGGG AGCCATCCCT TCCCTGTCCA CCTCACCAGG GGTGCTATGA

2001 CATGCAAGTG AGAAGCTGGG CATGAACGCA CTTTATAAAA GCAAAAGCTC

2051 TGTGTAAATC TAACTACAAG GACAATGCCT TGGGAGAGAT TTTGTCGGGA

2101 CAGAGAGGAG TTGCCAGGGA AGAAGGTTTG AAAGATACGG TTGTCTAGAG

2151 GTGAGACCAA AGGATCCAGA GACTTGGGGA CCAGAGGTGA CAGTGGATGA

2201 CGTGAAGCCA CAGGAGCCCC ACCCCCATGC AGCTTTTTCC CCACCCCCCC

2251 CACCACGCGC TCAATCATGA GTACCTCAAA GGATTGTTGG GCTTGGGGGA

2301 AAAGAGGTGG ATTCCTGGGC AAGAACCTAA AGTAGCAGGA (SEQ ID NO.11)

FIG.1B

```
     TCGAACTCACTCACCTCCCCTCTCACCTCACTGCCCTCACCAGCCAGCCTCTTGTCAAGT
  1  ------+---------+---------+---------+---------+---------+   60
     AGCTTGAGTGAGTGGAGGGGAGAGTGGAGTGACGGGAGTGGTCGGTCGGAGAACAGTTCA

GATCAGGCTGTCAACCAACTTCTCTAGGATAAGGTTTCAGGTCAGCCTGTGTATAAGA
 61  ------+---------+---------+---------+---------+---------+  120
     CTAGTCCGACAGTTGGTTGAAGAGATCCTATTCCAAAGTCCAGTCGGACACATATTCT

CCAGTGCCAAGCCAGAAGCAGAGACAACAGTGAATGACAAGGAGGGCCATCCAATC
121  ------+---------+---------+---------+---------+---------+  180
     GGTCACGGTTCGGTCTTCGTCTCTGTTGTCACTTACTGTTCCTCCCGGTACCTTAG

CCTGCTGCCACCTCCTGGGGATGGAGCCCTAGGGAGCCCCTGTGCTGCCCTGCCGTGGCA
181  ------+---------+---------+---------+---------+---------+  240
     GGACGACGGTGGAGGACCCTACCTCGGGATCCCTCGGGGACACGACGGGACGGCACCGT

GGACTCACAGCCCCACCGCTGCACTGAAGCCTGTGGAGCAGCTCTCTCCTTGGA
241  ------+---------+---------+---------+---------+---------+  300
     CCTGAGTGTCGGGGTGGCGACGTGACTTCGGGTCCCGACACTCGTGAGAGGAACCT

CTCCTCTCGGCCCTAAAGGGACTGGGCCAGAGCCTTCCAGGACTATGGTTGACTGAAGCC
301  ------+---------+---------+---------+---------+---------+  360
     GAGGAGAGCCGGGATTTCCCTGACCCGTCTCGGAAGGTCCTGATACCAACCTGACTTCGG
                                        M   V   G   L   K   P

TTCAGACGTGCCTCCCACCATGGCTGTGAAGTTCCTGGGGGCAGGCACAGCAGCCTGTTT
361  ------+---------+---------+---------+---------+---------+  420
     AAGTCTGCACGGAGGTGGTACCGACACTTCAAGGACCCCGTCCGTGTCGTCGGACAAA
       S   D   V   P   P   T   M   A   V   K   F   L   G   A   G   T   A   A   C   F

FIG.2A
```

```
421  TGCTGACCTCGTTACCTTTCCACTGGACACAGCCAAGGTCCGCCTGCAGATCCAGGGGGA
     ------+---------+---------+---------+---------+---------+  480
     ACGACTGGAGCAATGGAAAGGTGACCTGTGTCGTTCCAGGCGGACGTCTAGGTCCCCCT
      A  D  L  V  T  F  P  L  D  T  A  K  V  R  L  Q  I  Q  G  E

461  GAACCAGGCGGTCCAGACGGCCCGGCTCGTGCAGTACCGTGGCGTGCTGGGCACCATCCT
     ------+---------+---------+---------+---------+---------+  540
     CTTGGTCCGCCAGGTCTGCCGGGCCGAGCACGTCATGGCACCGCACGACCCGTGGTAGGA
      N  Q  A  V  Q  T  A  R  L  V  Q  Y  R  G  V  L  G  T  I  L

541  GACCATGGTGCGACTGAGGGTCCCTGCAGCCCCAGGGACGTCGGGGATGTTACCCGACCA
     ------+---------+---------+---------+---------+---------+  600
     CTGGTACCACGCTGACTCCCAGGGACGTCGGGGTCCCTGCAGCCCCTACAATGGGCTGGT
      T  M  V  R  T  E  G  P  C  S  P  Y  N  G  L  V  A  G  L  Q

601  GCGCCAGATGAGCTTCGCCTCATCAGATCGGCCTTTACGACTCCGTCAAGCAGGTGTA
     ------+---------+---------+---------+---------+---------+  660
     CGCGGTCTACTCGAAGCGGAGGTAGCGTAGCGGAAATGCTGAGGCAGTTCGTCCACAT
      R  Q  M  S  F  A  S  I  R  I  G  L  Y  D  S  V  K  Q  V  Y

661  CACCCCCAAAGGCGGGACAACTCCAGCCTCACTACCGGATTTTGGCCGCTGCACCAC
     ------+---------+---------+---------+---------+---------+  720
     GTGGGGTTTCCGCCTGTTGAGGTCGGAGTGATGGCCTAAAACCGGCGACGTGGTG
      T  P  K  G  A  D  N  S  S  L  T  T  R  I  L  A  G  C  T  T
```

FIG.2B

```
721  AGGAGCCATGGCGGTGACCTGTGCCCAGCCCACAGATGTGGTGAAGGTCCGATTTCAGGC
     ----------+---------+---------+---------+---------+---------+   780
     TCCTCGGTACCGCCACTGGACACGGGTCGGGTGTCTACACCACTTCCAGGCTAAAGTCCG
      G  A  M  A  V  T  C  A  Q  P  T  D  V  V  K  V  R  F  Q  A

781  CAGCATACACCCTCGGGCCATCCAGGAGGCGACAGAAAATACAGCGGGACTATGGACGCCTA
     ----------+---------+---------+---------+---------+---------+   840
     GTCGTATGTGGAGCCCGGTAGGTCCTCGCGTGTCTGTCTTTATGTCGCCCTGATACCTGGAT
      S  I  H  L  G  P  S  R  S  D  R  K  Y  S  G  T  M  D  A  Y

841  CAGAACCATCGCCAGGAGGAAGGAGTCAGGGGCCTGTGGAAAGGAACTTTGCCCAACAT
     ----------+---------+---------+---------+---------+---------+   900
     GTCTTGGTAGCGGTCCCTCCTTCCTCAGTCCCCGGACACCTTTCCTTGAAACGGGTTGTA
      R  T  I  A  R  E  E  G  V  R  G  L  W  K  G  T  L  P  N  I

901  CATGAGGAATGCTATCGTCAACTGTGCTGAACACTGACTACGACATCCTCAAGGAGAA
     ----------+---------+---------+---------+---------+---------+   960
     GTACTCCTTACGATAGCAGTTGACACGACTTGTGACTGATGCTGTAGGAGTTCCTCTT
      M  R  N  A  I  V  N  C  A  E  V  V  T  Y  D  I  L  K  E  K

961  GCTGCTGGACTATCACCTGCTCACTGACAACTTCCCCTGCCACTTTGTCTCTGCCTTTGG
     ----------+---------+---------+---------+---------+---------+   1020
     CGACGACCTGATAGTGGACGAGTGACTGTTGAAGGGGACGGTGAAACAGAGACGGAAACC
      L  L  D  Y  H  L  L  T  D  N  F  P  C  H  F  V  S  A  F  G

1021 AGCCGGGCTTCTGTGCCACAGTGGTGGCCTCCCCGGTGGACGTGGTGAAGACCCGGTATAT
     ----------+---------+---------+---------+---------+---------+   1080
     TCGGCCCGAAGACACGGTGTCACCACCGGAGGGGCCACCTGCACCACTTCTGGGCCATATA
      A  G  F  C  A  T  V  V  A  S  P  V  D  V  V  K  T  R  Y  M
```

FIG.2C

```
1081  GAACTCACCTCCCAGGCCAGTACTTCAGCCCCCTCGACTGTATGATAAAGATGGTGGCCCA
      ------+---------+---------+---------+---------+---------+  1140
      CTTGAGTGGAGGTCCGGTCATGAAGCTCGGGGGAGCTGACATACTATTTCTACCACGGGT
       N  S  P  P  G  Q  Y  F  S  P  L  D  C  M  I  K  M  V  A  Q

1141  GGAGGGCCCCACAGCCTTCTACAAGGGATTTACACCCTCCTTTTTGCGTTTGGGATCCTG
      ------+---------+---------+---------+---------+---------+  1200
      CCTCCCGGGGTGTCGGAAGATGTTCCCTAAATGTGGGAGGAAAAACGCAAACCCTAGGAC
       E  G  P  T  A  F  Y  K  G  F  T  P  S  F  L  R  L  G  S  W

1201  GAACGTGGTGATGTTCGTAACCTATGAGCAGCTGAAACGGGCCCTGATGAAAGTCCAGAT
      ------+---------+---------+---------+---------+---------+  1260
      CTTGCACCACTACAAGCATTGGATACTCGTCGACTTGCCCGGGACTACTTTCAGGTCTA
       N  V  M  F  V  T  Y  E  Q  L  K  R  A  L  M  K  V  Q  M

1261  GTTACGGGAATCACCGTTTTGAACAAGACAAGAAGGCCACTGGTAGCTAACGTGTCCGAA
      ------+---------+---------+---------+---------+---------+  1320
      CAATGCCCTTAGTGGCAAAACTTGTTCTGTTCTTCCGGTGACCATCGATTGCACAGGCTT
       L  R  E  S  S  P  F  *  (SEQ ID NO.12)

1321  ACCAGTTAAGAATGGAAGAAGAAAAACGGTGCATCCACGCACACATGGACACAGACCCACACAT
      ------+---------+---------+---------+---------+---------+  1380
      TGGTCAATTCTTACCTTCTTTTGCCACGTAGGTGCGTGTGTACCTGTGTCTGGGTGTGTA
```

FIG.2D

```
     GTTTACAGAACTGTTGTTGTTTACTTGTTGCTGATTCAAGAAACAGAAGTAGAAGAGAGAGGA
1381 ------+---------+---------+---------+---------+---------+---- 1440
     CAAATGTCTTGACAACAAATGAACAACGACTAAGTTCTTTGTCTTCATCTTCTCTCCT

TTCTGGTCTTCACTGCCATGCCTCAAGAACACCTTTGTTTTGCACTGACAAGATGGAAAA
1441 ------+---------+---------+---------+---------+---------+---- 1500
     AAGACCAGAAGTGACGGTACGGAGTTCTTGTGGAAACAAAACGTGACTGTTCTACCTTTT

TAAATTATATTAATTTTTGAAACCCATTAGGCATGCCTAATATTTAGGCAAGAGAAAATA
1501 ------+---------+---------+---------+---------+---------+---- 1560
     ATTTAATATAATTAAAAACTTTGGGTAATCGTACGGATTATAAATCGTTCTCTTTTAT

AACCAAGATAGATCCATTTGGACAAAATGGAAGGTTGGAGACGTGTATCCCGTGAAATC
1561 ------+---------+---------+---------+---------+---------+---- 1620
     TTGGTTCTATCTAGGTAAACCTGTTTTACCTTCCAACCTCTGCACATAGGGGCACTTTAG

TGGTCAGATAATGAATGATAAGCAGGAAGGATGGCAAGCACGGGACAGGAGGGGCCCACA
1621 ------+---------+---------+---------+---------+---------+---- 1680
     ACCAGTCTATTACTTACTATTCGTCCTTCCTACGGTTCGTGCCCTGTCCTCCCCGGGTGT

ATGGAGTGGGAGATCAGCCACGGAGCCTGGAGGGACGCGCCACCCAGCAACACAGAGCTGGC
1681 ------+---------+---------+---------+---------+---------+---- 1740
     TACCTCACCCTCTAGTCGGTGCCTCGGACCTCCCTGCGGTGGGTCGTTGTGTCTCGACCG

GACTGCAGCTGCACCATCACACATGCATCATCAGCCTATTTGTAATATGTCTGCCACAGA
1741 ------+---------+---------+---------+---------+---------+---- 1800
     CTGACGTCGACGTGGTAGTGTGTACGTAGTAGTCGGATAAACATTATACAGACGGTGTCT

GAGTCCTTTGGGATTCTAGGAAACCCAAGGAACAAGAGAAAAAACTAGAGCCTGTGCTAA
1801 ------+---------+---------+---------+---------+---------+---- 1860
     CTCAGGAAACCCTAAGATCCTTTGGGTTCCTTGTTCTCTTTTTGATCTCGGACACGATT
```

FIG.2E

```
1861  AGAAGCCTGCTGGGCCCATGTGAGGCTGGGGTCGTAAATATTCCCGACGACACTGAAGA
      ----+----+----+----+----+----+----+----+----+----+----+----+ 1920
      TCTTCGGACGACCGGGTACACTCCGACCCCAGCATTTATAAGGGGCTGCTGTGACTTCT

1921  ATCAAGAGGGCAGCCCCCACTTCTCCTACAAAATGGAGGGAGCCATCCCTTCCCTGTCCA
      ----+----+----+----+----+----+----+----+----+----+----+----+ 1980
      TAGTTCTCCCGTCGGGGGTGAAGAGGATGTTTTACCTCCCTCGGTAGGGAAGGGACAGGT

1981  CCTCACCAGGGGTGCTATGACATGCAAGTGAGAAGCTGGGCATGAACGCACTTTATAAAA
      ----+----+----+----+----+----+----+----+----+----+----+----+ 2040
      GGAGTGGTCCCCACGATACTGTACGTTCACTCTTCGACCGTACTTGCGTGAAATATTTT

2041  GCAAAAGCTCTGTGTAAATCTAACTACAAGGACACAATGCCTTGGGAGAGATTTGTCGGGA
      ----+----+----+----+----+----+----+----+----+----+----+----+ 2100
      CGTTTTCGAGACACATTTAGATTGATGTTCCTGTTACGGAACCCTCTCTAAAACAGCCCT

2101  CAGAGAGGAGTTGCCAGGGAAGAAGAAAGGTTTGAAAGATACGGTTGTCTAGAGGTGAGACCAA
      ----+----+----+----+----+----+----+----+----+----+----+----+ 2160
      GTCTCTCCTCAACGGTCCCTTCTTCCAAACTTTCTATGCCAACAGATCTCCACTCTGGTT

2161  AGGATCCAGAGACTTGGGGACCAGAGGTGACAGTGGATGACGTGAAGCCACAGGAGCCCC
      ----+----+----+----+----+----+----+----+----+----+----+----+ 2220
      TCCTAGGTCTCTGAACCCCTGGTCTCCACTGTCACCTACTGCACTTCGGTGTCCTCGGGG

2221  ACCCCCATGCAGCTTTTTCCCCACCCCCCCCACCACGGCGTCAATCATGAGTACCTCAAA
      ----+----+----+----+----+----+----+----+----+----+----+----+ 2280
      TGGGGTACGTCGAAAAAGGGGTGGGGGGGTGGTGCCGAGTTAGTACTCATGGAGTTT

2281  GGATTGTTGGGCTTGGGGGAAAAGAGGTGGATTCCTGGGCAAGAACCTAAAGTAGCAGGA
      ----+----+----+----+----+----+----+----+----+----+----+----+ 2340
      CCTAACAACCCGAACCCCTTTCTCCACCTAAGGACCCGTTCTTGGATTTCATCGTCCT
```

FIG.2F

```
  1 MVGLKPSSDP PTMAVKFLGA GTAACFADLV TFPLDTAKVR LQIQGENQAV
 51 QTARLVQYRG VLGTILTMVR TEGPCSPYNG LVAGLQRQMS FASIRIGLYD
101 SVKQVYTPKG ADNSSLTTRI LAGCTTGAMA VTCAQPTDVV KVRFQASIHL
151 GPSRSDRKYS GTMDAYRTIA REEGVRGLWK GTLPNIMRNA IVNCAEVVTY
201 DILKEKLLDY HLLTDNFPCH FVSAFGAGFC ATVVASPVDV VKTRYMNSPP
251 GQYFSPLDCM IKMVAQEGPT AFYKGFTPSF LRLGSWNVVM FVTYEQLKRA
301 LMKVQMLRES PF* (SEQ ID NO.12)
```

FIG.3

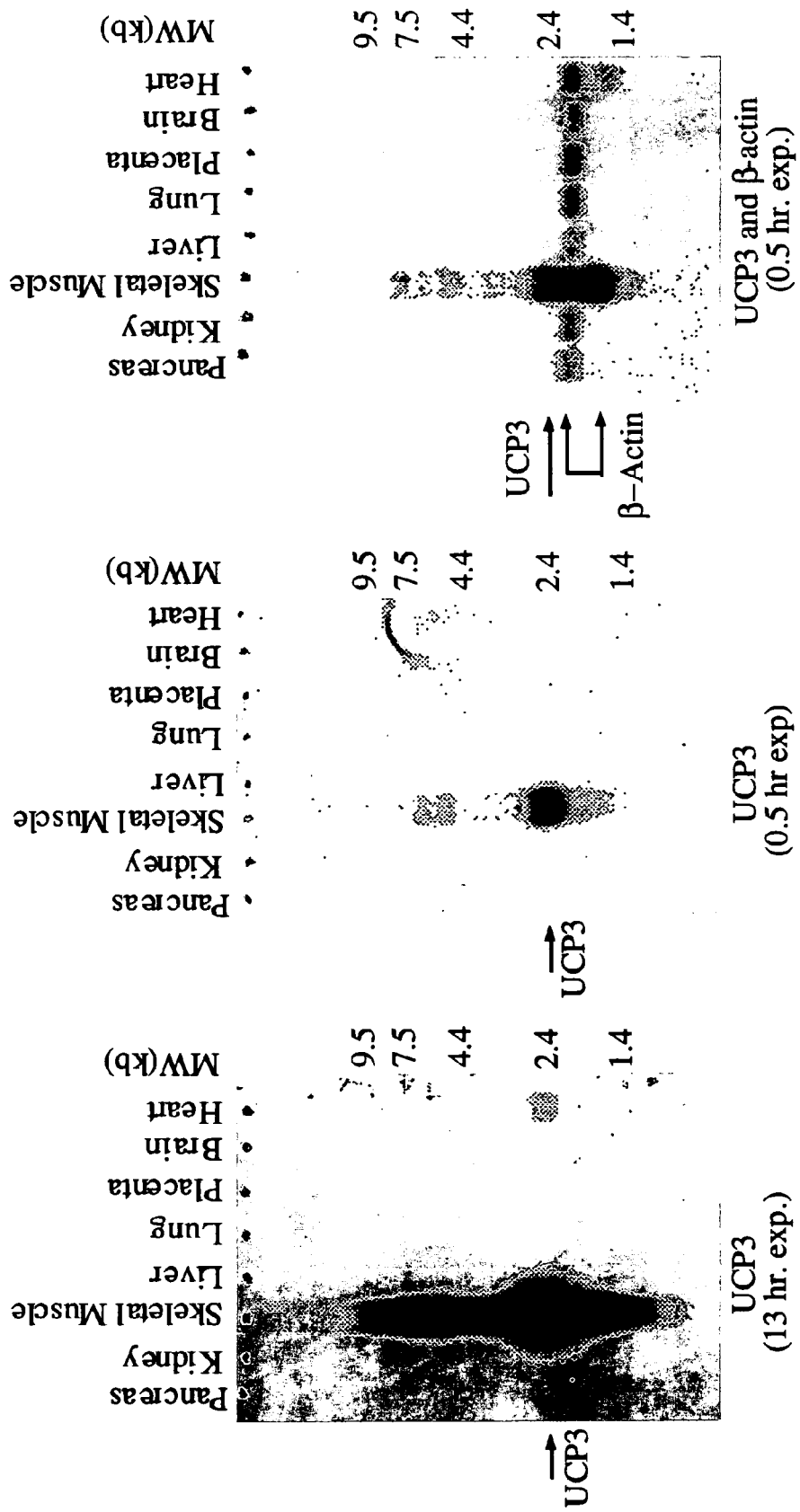

```
  1 CCAGGAACAG CAGAGACAAC AGTGAATGGT GAGGCCCGGC CGTCAGATCC
 51 TGCTGCTACC TAATGGAGTG GATCCTTAGG GTCGCCCTGC ACTACCCAAC
101 CTTGGCTAGA CGCACAGCTT CCTCCCTGAA CTGAAGCAAA AGATTGCCAG
151 CCAAGCTCTC TCCTCGGACC TCCATAGGCA GCAAAGGAAC CAGGCCCATT
201 CCCCGGGACC ATGGTTGGAC TTCAGCCCTC CGAAGTGCCT CCCACAACGG
251 TTGTGAAGTT CCTGGGGGCC GGCACTGCGG CCIGTTTTGC GGACCTCCTC
301 ACTTTTCCCC TGGACACCGC CAAGGTCCGT CTGCAGATCC AAGGGGAGAA
351 CCCAGGGGCT CAGAGCGTGC AGTACCGCGG TGTGCTGGGT ACCATCCTGA
401 CTATGGTGCG CACAGAGGGT CCCCGCAGCC CCTACAGCGG ACTGGTCGCT
451 GGCCTGCACC GCCAGATGAG TTTTGCCTCC ATTCGAATTG GCCTCTACGA
501 CTCTGTCAAG CAGTTCTACA CCCCCAAGGG AGCGGACCAC TCCAGCGTCG
551 CCATCAGGAT TCTGGCAGGC TGCACGACAG GAGCCATGGC AGTGACCTGC
601 GCCCAGCCCA CGGATGTGGT GAAGGTCCGA TTTCAAGCCA TGATACGCCT
651 GGGAACTGGA GGAGAGAGGA AATACAGAGG GACTATGGAT GCCTACAGAA
701 CCATCGCCAG GGAGGAAGGA GTCAGGGGCC TGTGGAAAGG GACTTGGCCC
751 AACATCACAA GAAATGCCAT TGTCAACTGT GCTGAGATGG TGACCTACGA
801 CATCATCAAG GAGAAGTTGC TGGAGTCTCA CCTGTTTACT GACAACTTCC
851 CCTGTCACTT TGTCTCTGCC TTTGGAGCTG GCTTCTGTGC CACAGTGGTG
901 GCCTCCCCGG TGGATGTGGT AAAGACCCGA TACATGAACG CTCCCCTAGG
951 CAGGTACCGC AGCCCTCTGC ACTGTATGCT GAAGATGGTG GCTCAGGAGG
```

FIG.6A

```
1001 GACCCACGGC CTTCTACAAA GGATTTGTGC CCTCCTTTCT GCGTCTGGGA

1051 GCTTGGAACG TGATGATGTT TGTAACATAT GAGCAACTGA AGAGGGCCTT

1101 AATGAAAGTC CAGGTACTGC GGGAATCTCC GTTTTGAACA AGGCAAGCAG

1151 GCTGCCTGGA ACAGAACAAA GCGTCTCTGC CCTGGGGACA CAGGCCCACA

1201 CGGTCCAGAA CCCTGCACTG CTGCTGACAC CAGAAACTGA ACTAAAAGAG

1251 GAGAGTTTTA GTCCTCCGTG TTTCGTCCTA AAACACCTCT GTTTTGCACT

1301 GACCTGATGG GAAATAAATT ATATTAATTT TTAAACCCTT TCCGGTTGGA

1351 TGCCTAACAT TTAGGCAAGA GACAACAAAG AAAACCAGAG TCAACTCCCT

1401 TGAAATGTAG GAATAAAGGA TGCATAATAA ACAGGAAAGG CACAGGTTTT

1451 GAGAAGATCA GCCCACAGTG TTGTCCTTGA ATCAAACAAA ATGGTCGGAG

1501 GAACCCTTCG GGTTCAGCAC AAAGAGGTGA CTACAGCCTT TTGGTCACCA

1551 GATGACTCCG CCCCTTTGTA ATGAGTCTGC CAAGTAGACT CTATCAAGAT

1601 TCTGGGGAAA GGAGAAAGAA CACATTGACC TGCCCGGGCG GCCGCTCGAG

1651 CCCTATGA (SEQ ID NO:17)
```

FIG.6B

```
  1 MVGLQPSEVP PTTVVRFLGA GTAACFADLL TFPLDTAKVR LQIQGENPGA
 51 QSVQYRGVLG TILTMVRTEG PRSPYSGLVA GLHRQMSFAS IRIGLYDSVK
101 QFYTPKGADH SSVAIRILAG CTTGAMAVTC AQPTDVVKVR FQAMIRLGTG
151 GERKYRGTMD AYRTIAREEG VRGLWKGTWP NITRNAIVNC AEMVTYDIIK
201 EKLLESHLFT DNFPCHFVSA FGAGFCATVV ASPVDVVKTR YMNAPLGRYR
251 SPLHCMLKMV AQEGPTAFYK GFVPSFLRLG AWNVMMFVTY EQLRRALMKV
301 QVLRESPF* (SEQ ID NO:18)
```

FIG.7

HUMAN UNCOUPLING PROTEIN 3

CROSS-REFERENCE TO RELATED APPLICATIONS

This application is a non-provisonal application of U.S. Provisional Application Ser. No. 60/069,141 filed Dec. 9, 1997, which is a continuation-in-part of U.S. Provisional Application Ser. No. 60/047,179, filed May 20, 1997.

STATEMENT REGARDING FEDERALLY-SPONSORED R&D

Not applicable.

REFERENCE TO MICROFICHE APPENDIX

Not applicable

FIELD OF THE INVENTION

The present invention relates to an isolated nucleic acid molecule (polynucleotide) which encodes a novel human uncoupling protein, referred to throughout as uncoupling protein 3 (UCP3). The present invention also relates to recombinant vectors and recombinant hosts which contain a DNA fragment encoding human UCP3, substantially purfied forms of associated human UCP3, human UCP3 mutant proteins, and methods associated with identifying compounds which modulate energy expenditure and body weight regulation, as well as affecting diseases such as obesity and diabetes.

BACKGROUND OF THE INVENTION

The balancing of energy expenditure and food intake plays a critical role in the control of body weight. Heat generation from uncoupling activity in mitochondria is responsible for a significant portion of energy expenditure, and therefore regulation of uncoupling activities provides a direct target for the treatment of obesity.

It is known that uncoupled mitochondrial respiration in brown adipose tissue (BAT) plays an important role in the regulation of energy balance in rodents.

Bouillaud et al. (1986, J. Biol. Chem. 261(4): 1487–1490) disclose a rat cDNA clone which encodes rat uncoupling protein 1 (UCP1). Rat UCP1 is a mitochondrial inner membrane protein synthesized in the cytosol from a nuclear encoded transcript which is expressed in brown adipose tissue.

Bouillaud et al. (1988, Biochem. Biophys Res. Comm. 157: 783–792) disclose a genomic clone encoding rat UCP1.

Nicholls and Locke (1984, Physiol. Rev. 64: 1–64) review UCP1, noting that the rat 32 kD protein forms a proton channel through the mitochondrial inner membrane and is active in uncoupling ATP synthesis from heat production in BAT.

Jacobsson et al. (1985, J. Biol. Chem. 260: 16250–16254) disclose cDNA clones for mRNA isolated from mouse brown adipose tissue. Mouse ucp1 mRNA was shown to be induced in brown adipose tissue by exposure to cold.

Kozak et al. (1988, J. Biol. Chem. 263: 12274–12277) disclose the genomic clone encoding mouse UCP1.

Cassard et al. (1990, J. Cell. Biochem. 43: 255–264) discloses the genomic clone for human ucp1, as well as the deduced amino acid sequence for human UCP1. The authors show that rat and human UCP1 are 79% homologous at both the nucleotide and amino acid level.

UCP1 activity in thermogenesis and uncoupled energy dissipation is limited to brown adipose tissue. Therefore, it is not expected that UCP1 is actively involved in the cause and effect of body weight indications such as obesity and diabetes in vertebrates such as humans, which contain limited amount of brown fat.

Fleury et al. (1997, Nature Genetics 15: 269–272) disclose a gene encoding both a mouse and human mitochondrial uncoupling protein, designated mouse UCP2 and human UCP2, respectively. The deduced human amino acid sequence encodes a 33 kD protein which is approximately 95% homologous to the mouse protein at the amino acid level. As with human UCP1, human UCP2 comprises 3 mitochondrial carrier protein motifs and an ATP binding site. The authors show a wide range of tissue specific expression of the human ucp2 gene, including skeletal muscle, lung, heart, placenta, stomach, as well as immune systems tissue such as spleen, thymus, leukocytes, macrophages and bone marrow. The authors mapped the human ucp2 gene to chromosome 11, which has been linked to obesity and hyperinsulinaemia in the mouse.

It would be advantageous to identify a gene encoding an additional human uncoupling protein wherein expression is for the most part limited to skeletal muscle. A nucleic acid molecule expressing an additional human uncoupling protein in such a specific manner would be extremely useful in screening for compounds acting as a modulator of to obesity and hyperinsulinaemia. Such a compound or compounds will be useful in controlling obesity as well as deleterious indications associated with obesity, such as diabetes. Additionally, such a nucleic acid molecule will be useful in gene therapy applications to overcome the deleterious effects of obesity and obesity-related complications, such as diabetes. The present invention addresses and meets this need.

SUMMARY OF THE INVENTION

The present invention relates to a purified or isolated nucleic acid molecule (polynucleotide) which encodes a novel vertebrate uncoupling protein.

The present invention relates to a purified or isolated nucleic acid molecule (polynucleotide) which encodes a novel human uncoupling protein.

The present invention also relates to a purified or isolated nucleic acid molecule which encodes a human uncoupling protein which is predominantly expressed within human skeletal muscle.

A preferred aspect of the present invention is disclosed in FIGS. 1A–1B and SEQ ID NO:11, a purified human cDNA encoding a novel uncoupling protein, UCP3.

Another specific embodiment of the present invention relates to isolated biologically active fragments or mutants of a nucleic acid molecule encoding human uncoupling protein 3, disclosed herein in FIGS. 2A–2D, FIG. 3 and SEQ ID NO:12. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use.

The present invention relates to a purified or isolated nucleic acid molecule (polynucleotide) which encodes a novel mouse uncoupling protein, as set forth as SEQ ID NO:17.

The present invention also relates to a purified or isolated nucleic acid molecule which encodes a mouse uncoupling protein which is predominantly expressed within human skeletal muscle, the expressed protein as set forth in SEQ ID NO:18.

The purified nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified mammalian nucleic acid molecules disclosed throughout this specification.

The present invention also relates to subcellular membrane fractions of the recombinant host cells (both prokaryotic and eukaryotic as well as both stably and transiently transformed cells) comprising the nucleic acids of the present invention. These subcellular membrane fractions will comprise UCP3 at levels substantially above wild type levels and hence will be useful in various assays described throughout this specification.

The present invention also relates to a substantially purified human uncoupling protein wherein the native form is substantially localized within mitochondria of skeletal muscle.

A preferred aspect of the present invention is disclosed in FIG. 2 and SEQ ID NO:12, the amino acid sequence of the exemplified human uncoupling protein, hUCP3.

Another preferred aspect of the present invention is disclosed in FIG. 7 and SEQ ID NO:18, the amino acid sequence of the exemplified mouse uncoupling protein, mUCP3.

The present invention also relates to biologically active fragments and/or mutants of a novel human uncoupling protein, including but not necessarily limited to amino acid substitutions, deletions, additions, amino terminal truncations and carboxy-terminal truncations such that these mutations provide for proteins or protein fragments of diagnostic, therapeutic or prophylactic use.

The present invention also relates to methods of expressing the UCP proteins or protein fragments disclosed herein, assays employing these human UCPs, cells expressing these UCPs, and compounds identified through the use of these UCPs, including modulators of energy expenditure and body weight regulation, either through direct contact with the mitochondrial uncoupling protein, or a compound which acts in trans to modulate UCP expression. Such modulators identified in this process are useful as therapeutic agents for controlling obesity, diabetes and other related diseases.

BRIEF DESCRIPTION OF THE DRAWINGS

FIG. 1A and FIG. 1B show the nucleotide sequence (SEQ ID NO:11) which comprises the full-length cDNA encoding human uncoupling protein 3.

FIG. 2A, FIG. 2B, FIG. 2C and FIG. 2D show the translation of the open reading frame (SEQ ID NO:12) of the full-length human uncoupling protein 3 nucleotide sequence.

FIG. 3 shows the amino acid sequence of human uncoupling protein 3 (SEQ ID NO:12).

FIG. 4A, FIG. 4B and FIG. 4C show Northern blot analysis of human uncoupling protein 3 in human tissue.

FIGS. 6A and 6B shows the nucleotide sequence (SEQ ID NO:17) of a cDNA which encodes the full-length mouse uncoupling protein 3.

FIG. 7 shows the amino acid sequence (SEQ ID NO:18) of the mouse uncoupling protein 3.

FIG. 9A shows measurement of weight loss. Y-axis indicates the average weight expressed in percentage of weight releative to the day of injection (Day 0). FIG. 9B shows UCP3 mRNA level. Y-axis indicates the relative level of UCP3 mRNA (the average of the Adb-gal and control animals is assigned a value of 1). Standard deviation for each group is as marked. Ad-Leptin: first generation E1-deleted, replication deficient adenoviral vector expressing leptin; HD-leptin: helper-dependent adenoviral vector expressing leptin; Adb-gal: first generation adenoviral vector expressing b-galactosidase; Control: untreated.

DETAILED DESCRIPTION OF THE INVENTION

Figure 5:
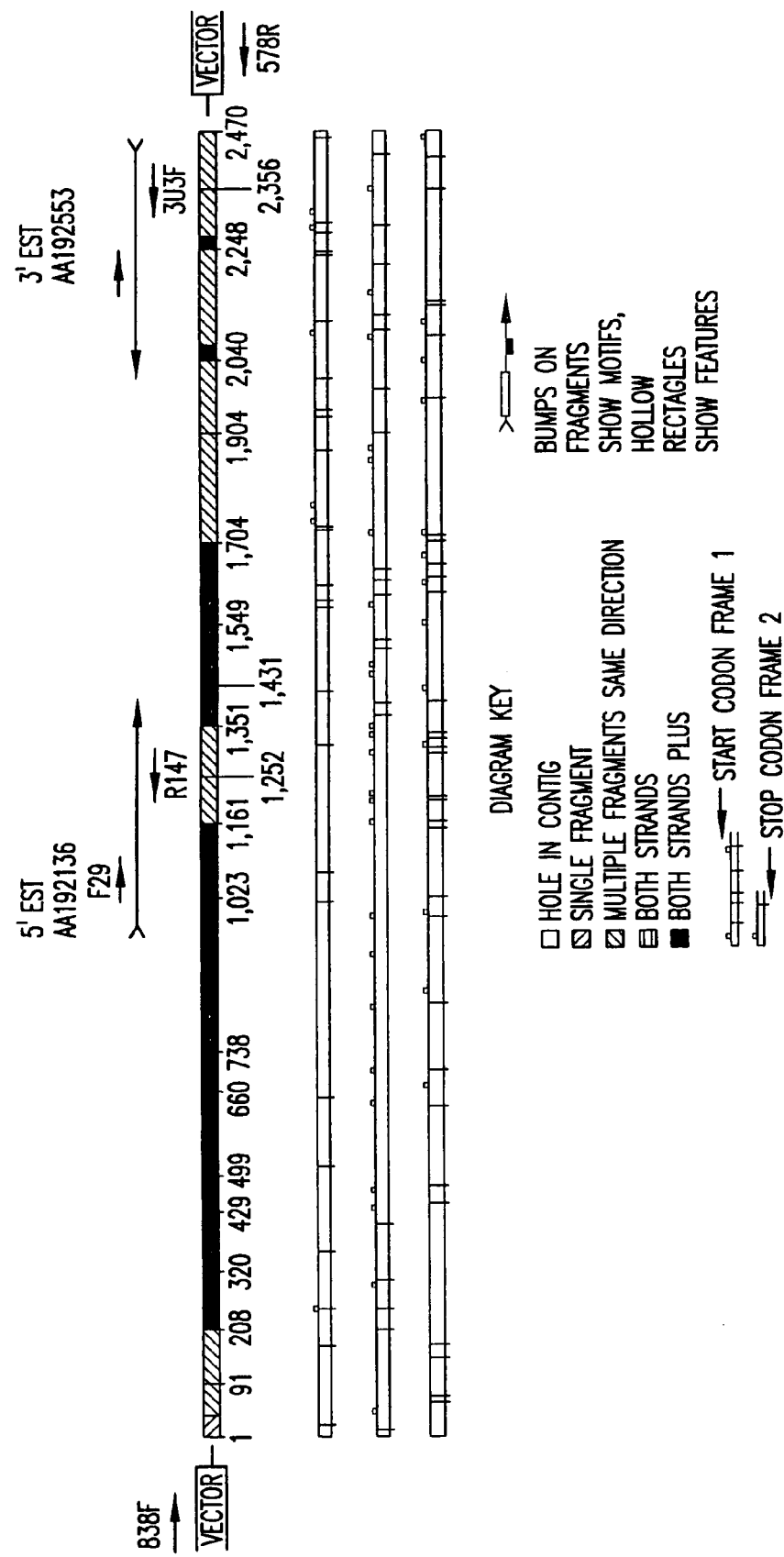
FIG. 5 shows the orientation of vector and gene specific primers used to screen a human fetal brain cDNA library for a full-length human UCP3 cDNA.

The present invention relates to isolated nucleic acid and protein forms which represent a vertebrate uncoupling protein, preferably human and mouse forms. The isolated genes and concomitant translation products which make up a portion of the present invention may be used in various ways in the treatment of obesity and other related diseases, including but not limited to diabetes. The uncoupling protein of the present invention is a protein which is translated in the cytosol from a nuclear encoded mRNA transcript. This uncoupling protein is presumably imported into the mitochondrial inner membrane post-translationally.

The process of oxidative phosphorylation pumps protons to the outside of the inner membrane of the mitochondria, leading to the generation of a membrane potential across the inner membrane. This membrane potential is then used to drive ATP synthesis. The purified uncoupling proteins of the present invention have the ability to uncouple the protonmotive force associated with oxidative phosphorylation, resulting in the concomitant release of large amounts of energy. It will be within the scope of the present invention to use the herein disclosed nucleic acids to construct recombinant vectors and recombinant host cells wherein the human UCP3 gene is expressed, either stably or transiently. Such transformed recombinant cell lines will be useful in screening for modulators of UCP3 activity, and hence, as effectors of energy expenditure and body weight regulation. The isolated nucleic acid fragments of the present invention will also be useful in gene therapy applications regarding therapeutic treatment of obesity and obesity related indications, including but not limited to diabetes, as well as conditions such as mitochondrial-associated hypermetabolism.

To this end, the present invention relates to a purified or isolated nucleic acid molecule (polynucleotide) which encodes a novel human uncoupling protein.

The present invention also relates to a purified or isolated nucleic acid molecule which encodes a human uncoupling protein which is predominantly expressed within human skeletal muscle.

A preferred aspect of the present invention is disclosed in FIG. 1 and SEQ ID NO:11, a purified human cDNA encoding a novel uncoupling protein, UCP3, which is as follows:

```
TCGAACTCAC TCACCTCCCC TCTCACCTCA CTGCCCTCAC CAGCCAGCCT (SEQ ID NO:11).

CTTGTCAAGT GATCAGGCTC TCAACCAACT TCTCTAGGAT AAGGTTTCAG

GTCAGCCTGT GTGTATAAGA CCAGTGCCAA GCCAGAAGCA GCAGAGACAA

CAGTGAATGA CAAGGAGGGG CCATCCAATC CCTGCTGCCA CCTCCTGGGA

TGGAGCCCTA GGGAGCCCCT GTGCTGCCCC TGCCGTGGCA GGACTCACAG

CCCCACCGCT GCACTGAAGC CCAGGGCTGT GGAGCAGCTC TCTCCTTGGA

CTCCTCTCGG CCCTAAAGGG ACTGGGCAGA GCCTTCCAGG ACTATGGTTG

GACTGAAGCC TTCAGACGTG CCTCCCACCA TGGCTGTGAA GTTCCTGGGG

GCAGGCACAG CAGCCTGTTT TGCTGACCTC GTTACCTTTC CACTGGACAC

AGCCAAGGTC CGCCTGCAGA TCCAGGGGGA GAACCAGGCG GTCCAGACGG

CCCGGCTCGT GCAGTACCGT GGCGTGCTGG GCACCATCCT GACCATGGTG

CGGACTGAGG GTCCCTGCAG CCCCTACAAT GGGCTGGTGG CCGGCCTGCA

GCGCCAGATG AGCTTCGCCT CCATCCGCAT CGGCCTTTAC GACTCCGTCA

AGCAGGTGTA CACCCCCAAA GGCGCGGACA ACTCCAGCCT CACTACCCGG

ATTTTGGCCG GCTGCACCAC AGGAGCCATG GCGGTGACCT GTGCCCAGCC

CACAGATGTG GTGAAGGTCC GATTTCAGGC CAGCATACAC CTCGGGCCAT

CCAGGAGCGA CAGAAAATAC AGCGGGACTA TGGACGCCTA CAGAACCATC

GCCAGGGAGG AAGGAGTCAG GGGCCTGTGG AAAGGAACTT TGCCCAACAT

CATGAGGAAT GCTATCGTCA ACTGTGCTGA GGTGGTGACC TACGACATCC

TCAAGGAGAA GCTGCTGGAC TATCACCTGC TCACTGACAA CTTCCCCTGC

CACTTTGTCT CTGCCTTTGG AGCCGGCTTC TGTGCCACAG TGGTGGCCTC

CCCGGTGGAC GTGGTGAAGA CCCGGTATAT GAACTCACCT CCAGGCCAGT

ACTTCAGCCC CCTCGACTGT ATGATAAAGA TGGTGGCCCA GGAGGGCCCC

ACAGCCTTCT ACAAGGGATT TACACCCTCC TTTTTGCGTT TGGGATCCTG

GAACGTGGTG ATGTTCGTAA CCTATGAGCA GCTGAAACGG GCCCTGATGA

AAGTCCAGAT GTTACGGGAA TCACCGTTTT GAACAAGACA AGAAGGCCAC

TGGTAGCTAA CGTGTCCGAA ACCAGTTAAG AATGGAAGAA AACGGTGCAT

CCACGCACAC ATGGACACAG ACCCACACAT GTTTACAGAA CTGTTGTTTA

CTTGTTGCTG ATTCAAGAAA CAGAAGTAGA AGAGAGAGGA TTCTGGTCTT

CACTGCCATG CCTCAAGAAC ACCTTTGTTT TGCACTGACA AGATGGAAAA

TAAATTATAT TAATTTTTGA AACCCATTAG GCATGCCTAA TATTTAGGCA

AGAGAAAATA AACCAAGATA GATCCATTTG GACAAAATGG AAGGTTGGAG

ACGTGTATCC CCGTGAAATC TGGTCAGATA ATGAATGATA AGCAGGAAGG

ATGGCAAGCA CGGGACAGGA GGGGCCCACA ATGGAGTGGG AGATCAGCCA

CGGAGCCTGG AGGGACGCCA CCCAGCAACA CAGAGCTGGC GACTGCAGCT
```

```
                                                    -continued
GCACCATCAC ACATGCATCA TCAGCCTATT TGTAATATGT CTGCCACAGA

GAGTCCTTTG GGATTCTAGG AAACCCAAGG AACAAGAGAA AAAACTAGAG

CCTGTGCTAA AGAAGCCTGC TGGGCCCATG TGAGGCTGGG GTCGTAAATA

TTCCCCGACG ACACTGAAGA ATCAAGAGGG CAGCCCCCAC TTCTCCTACA

AAATGGAGGG AGCCATCCCT TCCCTGTCCA CCTCACCAGG GGTGCTATGA

CATGCAAGTG AGAAGCTGGG CATGAACGCA CTTTATAAAA GCAAAAGCTC

TGTGTAAATC TAACTACAAG GACAATGCCT TGGGAGAGAT TTTGTCGGGA

CAGAGAGGAG TTGCCAGGGA AGAAGGTTTG AAAGATACGG TTGTCTAGAG

GTGAGACCAA AGGATCCAGA GACTTGGGGA CCAGAGGTGA CAGTGGATGA

CGTGAAGCCA CAGGAGCCCC ACCCCCATGC AGCTTTTTCC CCACCCCCCC

CACCACGCGC TCAATCATGA GTACCTCAAA GGATTGTTGG GCTTGGGGGA

AAAGAGGTGG ATTCCTGGGC AAGAACCTAA AGTAGCAGGA
```

Another specific embodiment of the present invention relates to isolated biologically active fragments or mutants of a nucleic acid molecule encoding human uncoupling protein 3, disclosed herein as SEQ ID NO:11 (see also FIGS. 1A–1B). Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use.

The purified nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification.

The present invention also relates to a substantially purified human uncoupling protein wherein the native form is substantially localized within mitochondria of skeletal muscle.

A preferred aspect of the present invention is disclosed in FIGS. 2A–2D, FIG. 3 and SEQ ID NO:12, the amino acid sequence of the exemplified human uncoupling protein, UCP3, which is as follows:

MVGLKPSDVPPTMAVKFLGAGTAAC-
FADLVTFPLDTAKVRLQIQGENQAVQTARLV QYRGV-
LGTILTMVRTEGPCSPYNGLVA-
GLQRQMSFASIRIGLYDSVKQVYTPKGAD
NSSLTTRILAGCTTGAMAVTCAQPTDV-
VKVRFQASIHLGPSRSDRKYSGTMDAYRT IAREE-
GVRGLWKGTLPNIMRNAIVNCAEVVTY-
DILKEKLLDYHLLTDNFPCHFVSA
FGAGFCATVVASPVDVVKTRYMNSP-
PGQYFSPLDCMIKMVAQEGPTAFYKGFTPSF LRLG-
SWNVVMFVTYEQLKRALMKVQMLRESPF, as set forth in three-letter abbreviation in SEQ ID NO:12.

The present invention also relates to biologically active fragments and/or mutants of a novel human uncoupling protein, including but not necessarily limited to amino acid substitutions, deletions, additions, amino terminal truncations and carboxy-terminal truncations such that these mutations provide for proteins or protein fragments of diagnostic, therapeutic or prophylactic use.

The present invention also relates to methods of expressing the vertebrate UCP proteins or protein fragments disclosed herein, assays employing these human and mouse UCPs, cells expressing these UCPs, and compounds identified through the use of these UCPs, including modulators of energy expenditure and body weight regulation, either through direct contact with the mitochondrial uncoupling protein, or a compound which acts in trans to modulate ucp expression. Such modulators identified in this process are useful as therapeutic agents for controlling obesity, diabetes and other related diseases.

Other uses of the nucleic acid fragment and protein fragments of the present invention include, but are not limited to, identifiying transacting factors which regulate UCP3 expression. It will then be possible to identify compounds which affect a protein or protein complex acting in trans to up or down regulate vertebrate UCP3 expression such that administration of such a compound or pharmaceutically acceptable salt in a pharmaceutically acceptable formulation will modulate UCP3 expression and in turn the degree of energy expenditure within the patient. It will be known to one of skill in the art that use of such an assay may proceed by construction of a prokaryotic or eukaryotic expression vector wherein a portion of the UPC3 5' noncoding region is fused to an appropriate reporter gene (including but not limited to β-galactosidase) which is utilized to quantitatively measure the effect of a particular compound on UPC3 gene regulation. It will also be possible to identify compounds through screens utilizing recombinant host cells stably or transiently transfected with a UPC3 encoding gene fragment. These compounds will affect, for example, the level of uncoupling of oxidative phosophorylation from ATP synthesis in mitochondria of transfected cells.

Therefore, the present invention also relates to methods of expressing a nucleic acid fragment encoding UCP, including but not limited to the exemplified human and/or mouse ucp3 or gene fragments disclosed herein, recombinant prokaryotic and eukaryotic expression vectors containing such a nucleic acid fragment, recombinant host cells transfected with these vectors wherein a ucp gene or gene fragment is expressed at predetermined levels through appropriate vector construction, and compounds identified through the interaction with either regulatory regions of a ucp gene or a compound which interacts with the mature, mitochondrial-localized form of a UCP protein. Such a compound may be useful in treating disorders associated with regulation of body weight and concomitant intake and expeniture of energy (or lack thereof), including but not limited to obesity and diabetes.

To this end, the present invention also relates to a purified or isolated nucleic acid molecule (polynucleotide) which encodes a novel mouse uncoupling protein, as set forth as SEQ ID NO:17, and as follows:

```
CCAGGAACAG CAGAGACAAC AGTGAATGGT GAGGCCCGGC CGTCAGATCC  disclosed as SEQ ID NO:17.

TGCTGCTACC TAATGGAGTG GATCCTTAGG GTGGCCCTGC ACTACCCAAC

CTTGGCTAGA CGCACAGCTT CCTCCCTGAA CTGAAGCAAA AGATTGCCAG

GCAAGCTCTC TCCTCGGACC TCCATAGGCA GCAAAGGAAC CAGGCCCATT

CCCCGGGACC ATGGTTGGAC TTCAGCCCTC CGAAGTGCCT CCCACAACGG

TTGTGAAGTT CCTGGGGGCC GGCACTGCGG CCTGTTTTGC GGACCTCCTC

ACTTTTCCCC TGGACACCGC CAAGGTCCGT CTGCAGATCC AAGGGGAGAA

CCCAGGGGCT CAGAGCGTGC AGTACCGCGG TGTGCTGGGT ACCATCCTGA

CTATGGTGCG CACAGAGGGT CCCCGCAGCC CCTACAGCGG ACTGGTCGCT

GGCCTGCACC GCCAGATGAG TTTTGCCTCC ATTCGAATTG GCCTCTACGA

CTCTGTCAAG CAGTTCTACA CCCCCAAGGG AGCGGACCAC TCCAGCGTCG

CCATCAGGAT TCTGGCAGGC TGCACGACAG GAGCCATGGC AGTGACCTGC

GCCCAGCCCA CGGATGTGGT GAAGGTCCGA TTTCAAGCCA TGATACGCCT

GGGAACTGGA GGAGAGAGGA AATACAGAGG GACTATGGAT GCCTACAGAA

CCATCGCCAG GGAGGAAGGA GTCAGGGGCC TGTGGAAAGG GACTTGGCCC

AACATCACAA GAAATGCCAT TGTCAACTGT GCTGAGATGG TGACCTACGA

CATCATCAAG GAGAAGTTGC TGGAGTCTCA CCTGTTTACT GACAACTTCC

CCTGTCACTT TGTCTCTGCC TTTGGAGCTG GCTTCTGTGC CACAGTGGTG

GCCTCCCCGG TGGATGTGGT AAAGACCCGA TACATGAACG CTCCCCTAGG

CAGGTACCGC AGCCCTCTGC ACTGTATGCT GAAGATGGTG GCTCAGGAGG

GACCCACGGC CTTCTACAAA GGATTTGTGC CCTCCTTTCT GCGTCTGGGA

GCTTGGAACG TGATGATGTT TGTAACATAT GAGCAACTGA AGAGGGCCTT

AATGAAAGTC CAGGTACTGC GGGAATCTCC GTTTTGAACA AGGCAAGCAG

GCTGCCTGGA ACAGAACAAA GCGTCTCTGC CCTGGGACA CAGGCCCACA

CGGTCCAGAA CCCTGCACTG CTGCTGACAC GAGAAACTGA ACTAAAAGAG

GAGAGTTTTA GTCCTCCGTG TTTCGTCCTA AAACACCTCT GTTTTGCACT

GACCTGATGG GAAATAAATT ATATTAATTT TTAAACCCTT TCCGGTTGGA

TGCCTAACAT TTAGGCAAGA GACAACAAAG AAAACCAGAG TCAACTCCCT

TGAAATGTAG GAATAAAGGA TGCATAATAA ACAGGAAAGG CACAGGTTTT

GAGAAGATCA GCCCACAGTG TTGTCCTTGA ATCAAACAAA ATGGTCGGAG

GAACCCTTCG GGTTCAGCAC AAAGAGGTGA CTACAGCCTT TTGGTCACCA

GATGACTCCG CCCCTTTGTA ATGAGTCTGC CAAGTAGACT CTATCAAGAT

TCTGGGGAAA GGAGAAAGAA CACATTGACC TGCCCGGGCG GCCGCTCGAG

CCCTATGA,
```

The present invention also relates to mouse forms of isolated biologically active fragments or mutants of a nucleic acid molecule encoding human uncoupling protein 3, disclosed herein as SEQ ID NO:17 (see also FIGS. 6A–6B). Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use.

The purified mouse nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified mouse nucleic acid molecules disclosed throughout this specification.

The present invention also relates to a substantially purified mouse uncoupling protein wherein the native form is substantially localized within mitochondria of skeletal muscle.

A preferred aspect of the present invention is disclosed in FIG. 7 and SEQ ID NO:18, the amino acid sequence of the exemplified mouse uncoupling protein, UCP3, which is as follows:

```
MVGLQPSEVP PTTVVKFLGA GTAACFADLL TFPLDTAKVR LQIQGENPGA
QSVQYRGVLG TILTMVRTEG PRSPYSGLVA GLHRQMSFAS IRIGLYDSVK
QFYTPKGADH SSVAIRILAG CTTGAMAVTC AQPTDVVKVR FQAMIRLGTG
GERKYRGTMD AYRTIAREEG VRGLWKGTWP NITRNAIVNC AEMVTYDIIK
EKLLESHLFT DNFPCHFVSA FGAGFCATVV ASPVDVVKTR YMNAPLGRYR
SPLHCMLKMV AQEGPTAFYK GFVPSFLRLG AWNVMMFVTY EQLKRALMKV
QVLRESPF*,
``` as set forth in three-letter abbreviation in SEQ ID NO:18.

The present invention also relates to biologically active fragments and/or mutants of a novel mouse uncoupling protein, including but not necessarily limited to amino acid substitutions, deletions, additions, amino terminal truncations and carboxy-terminal truncations such that these mutations provide for proteins or protein fragments of diagnostic, therapeutic or prophylactic use.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

As used herein, "purified" and "isolated" are utilized interchangibly to stand for the proposititition that the nucleic acid, protein, or respective fragment thereof in question has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in pure quantities so as to afford the opportunity to generate polyclonal antibodies, monoclononal antibodies, amino acid sequencing, and peptide digestion. Therefore, the nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

As used herein, "UCP3" may refer to any vertebrate form of UCP3, including but not limited to mouse or human UCP3.

As used herein, "BAT" means brown adipose tissue.

As used herein, "EST" means expressed sequence tag.

As used herein, a "biologically active equivalent" or "functional derivative" of a wild type UCP3 possesses a biological activity that is substantially similar to the biological activity of the wild type UCP3. The term "functional derivative" is intended to include the "fragments," "mutants," "variants," "degenerate variants," "analogs" and "homologues" or to "chemical derivatives" of the wild type UCP3 protein. The term "fragment" is meant to refer to any polypeptide subset of wild type UCP3. The term "mutant" is meant to refer to a molecule that may be substantially similar to the wild type form but possesses distinguishing biological characteristics. Such altered characteristics include but are in no way limited to altered substrate binding, altered substrate affinity and altered sensitivity to chemical compounds affecting biological activity of the UCP3 or UCP3 functional derivative. The term "variant" is meant to refer to a molecule substantially similar in structure and function to either the entire wild type protein or to a fragment thereof A molecule is "substantially similar" to a wild type UCP3-like protein if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire wild type UCP3-like protein or to a fragment thereof.

Any of a variety of procedures may be used to clone UCP3. These methods include, but are not limited to, (1) a RACE PCR cloning technique (Frohman, et al., 1988, *Proc. Natl. Acad. Sci.*85: 8998–9002). 5' and/or 3' RACE may be performed to generate a full length cDNA sequence. This strategy involves using gene-specific oligonucleotide primers for PCR amplification of UCP3 cDNA. These gene-specific primers are designed through identification of an expressed sequence tag (EST) nucleotide sequence which has been identified by searching any number of publicly available nucleic acid and protein databases; (2) direct functional expression of the UCP3 cDNA following the construction of an UCP3-containing cDNA library in an appropriate expression vector system; (3) screening a UCP3-containing cDNA library constructed in a bacteriophage or plasmid shuttle vector with a labeled degenerate oligonucleotide probe designed from the amino acid sequence of the UCP3 protein; (4) screening a UCP3-containing cDNA library constructed in a bacteriophage or plasmid shuttle vector with a partial cDNA encoding the UCP3 protein. This partial cDNA is obtained by the specific PCR amplification of UCP3 DNA fragments through the design of degenerate oligonucleotide primers from the amino acid sequence known for other UCP3 kinases which are related to the UCP3 protein; (5) screening an UCP3-containing cDNA library constructed in a bacteriophage or plasmid shuttle vector with a partial cDNA encoding the UCP3 protein. This strategy may also involve using gene-specific oligonucleotide primers for PCR amplification of UCP3 cDNA identified as an EST as described above; or (6) designing 5' and 3' gene specific oligonucleotides using SEQ ID NOS 1 or 2 as a template so that either the full length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full length version of the nucleotide sequence encoding UCP3.

It is readily apparent to those skilled in the art that other types of libraries, as well as libraries constructed from other cells types or species types, may be useful for isolating a UCP3-encoding DNA or a UCP3 homologue. Other types of libraries include, but are not limited to, cDNA libraries derived from other cells or cell lines other than human cells or tissue such as murine cells, rodent cells or any other such vertebrate host which may contain a UCP3-encoding DNA. Additionally a UCP3 gene may be isolated by oligonucleotide- or polynucleotide-based hybridization screening of a vertebrate genomic library, including but not limited to a human genomic library, a murine genomic library and a rodent genomic library, as well as concomitant human genomic DNA libraries.

It is readily apparent to those skilled in the art that suitable cDNA libraries may be prepared from cells or cell lines which have UCP3 activity. The selection of cells or cell lines for use in preparing a cDNA library to isolate a UCP3 cDNA may be done by first measuring cell associated UCP3 activity using any known assay for UCP3 activity.

Preparation of cDNA libraries can be performed by standard techniques well known in the art. Well known cDNA library construction techniques can be found for example, in Sambrook, et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagent.

It is also readily apparent to those skilled in the art that DNA encoding UCP3 may also be isolated from a suitable genomic DNA library. Construction of genomic DNA libraries can be performed by standard techniques well known in the art. Well known genomic DNA library construction techniques can be found in Sambrook, et al., supra.

In order to clone the UCP3 gene by one of the preferred methods, the amino acid sequence or DNA sequence of UCP3 or a homologous protein may be necessary. To accomplish this, the UCP3 or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial UCP3 DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the UCP3 sequence but others in the set will be capable of hybridizing to UCP3 DNA even in the presence of DNA oligonucleotides with mismatches. The mismatched DNA oligonucleotides may still sufficiently hybridize to the UCP3 DNA to permit identification and isolation of UCP3 encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NOS: 1 or 2, either for the purpose of isolating overlapping 5' and 3' RACE products for generation of a full-length sequence coding for UCP3, or to isolate a portion of the nucleotide sequence coding for UCP3 for use as a probe to screen one or more cDNA- or genomic-based libraries to isolate a full-length sequence encoding UCP3 or UCP3-like proteins.

In an exemplified method, the human UCP3 full length cDNA of the present invention was generated by a novel method of cDNA screening. Briefly, the extension of partial cDNA sequences have historically been achieved with one or both of the two commonly used methods: filter screening of cDNA libraries by hybridization with labeled probes, and 5'- and 3'-RACE with total cellular mRNA by PCR. The first method is effective but laborious and slow while the latter method is fast but limited in efficiency. This RACE protocol is hindered by limited length of extension due to the use of the entire cellular mRNA population in a single reaction. Since smaller fragments are amplified much more efficiently than larger fragments by PCR in the same reaction, PCR products obtained using the second method are often quite small. This portion of the present invention marks an improvement upon known methods of cDNA library screening by initially constructing and subdividing cDNA libraries followed by isolating 5'- and 3'-flanking fragments by PCR. Since each pool is unlikely to contain more than one clone for a given gene which is low to moderately expressed, competition between large and small PCR products in one pool does not exist, making it possible to isolate fragments of various sizes. One defininte advantage of the method disclosed in this specification is the efficiency, throughput, and its potential to isolate alternatively spliced cDNA forms.

Therefore, this portion of the invention relates to a process for rapid extension of a partial cDNA sequence based on subdividing a primary cDNA library and DNA amplification by polymerase chain reaction (PCR). A cDNA library is constructed with cDNA primed by random, oligo-dT or a combination of both random and oligo-dT primers and then subdivided into pools at approximately 10,000–20,000 clones per pool. Each pool is amplified separately and therefore represents an independent portion of the cDNA molecules from the original mRNA source. Samples from all the pools are collected and transferred into 96-well plates. To extend a partial cDNA sequence, such as SEQ ID NO:1 or 2, positive pools containing the partial cDNA sequence are first identified by PCR with a pair of primers complementary to the cDNA sequence. Each positive pool in the library contains an independent clone of the cDNA sequence; within each clone are embedded the partial cDNA sequence and its flanking fragments. The flanking fragments are isolated by PCR with primers complementary to the known vector and cDNA sequences and then sequenced directly. The DNA sequences from these fragments plus the original partial cDNA sequence are assembled into a continuous fragment, resulting in the extension of the partial cDNA sequence and the eventual determination of its full-length gene sequence by repeating the process, if necessary, until a complete open reading frame is obtained.

The fundamental principle of this process is to subdivide a complex library into pools of about 10,000 to about 20,000 clones. A library of two million primary clones, a number large enough to cover most mRNA transcripts expressed in the tissue, can be subdivided into 188 pools and stored in two 96-well plates. Since the number of transcripts for most genes is fewer than one copy per ~10,000 transcripts in total cellular mRNA, each pool is unlikely to contain more than one clone for a given cDNA sequence. Such reduced complexity makes it possible to use PCR to isolate flanking fragments of partial cDNA sequences larger than those obtained by known methods.

The foregoing process is exemplifed for isolation and characterization of a full-length cDNA encoding human UCP3. Briefly, a random and oligo dT primed fetal brain cDNA library consisting of approximately 4 million primary clones was constructed in the plasmid vector pBluescript (Stratagene, LaJolla, Calif.). The primary clones were subdivided into 188 pools with each pool containing ~20,000 clones. Each pool was amplified separately and the resulting plasmid pools were collected and transferred into two 96-well plates. Primer pairs from the 5' and 3' portion of SEQ ID NO:1 (EST-AA192136), 5' and 3' oligonucleotides from SEQ ID NO:4 (EST-AA192553) as well as oligonucleotide primers both 5' and 3' of the polylinker sequence of the vector (in this case, pBluescript SK⁻) were used to scan this human fetal brain cDNA library distributed in a 96-well plate separately. Initial positive pools were identifed with the 5' and 3' primers from AA192136 (SEQ ID NOS: 5 and 6) and the pBluescript primers (SEQ ID NOS:9 and 10). The positive pools were scanned again by PCR with both pBluescript primers as well as the 5' and 3' primers associated with the 3' EST, AA192553 (primers 3U3F and 3U3R). This step showed that scanning with 838F (pBSK⁻, SEQ ID NO: 9) and 3U3F (hybridizing to the 3' EST AA192553; SEQ ID NO:8), generated a 2.4 Kb cDNA fragment. This cDNA fragment was subcloned into the vector pTA2.1 (Invitrogen, San Diego, Calif., USA) by TA cloning. Four positive clones, the original PCR fragment, as well the I.M.A.G.E. clone #628529 (SEQ ID NOS:1 and 2) were sequenced by primer walking. The sequences were then assembled into a contig of 2340 base pairs which is as set forth in SEQ ID NO:11 and FIG. 1A and FIG. 1B. This sequence contains an open reading frame that encodes a polypeptide of 312 amino acids as set forth in SEQ ID NO:12 and FIGS. 2A–2D and FIG. 3.

The cDNA as set forth in SEQ ID NO:11 was identified as a full-length cDNA fragment from a single positive pool. FIG. 5 shows the vector and EST (gene) specific primers used to isolate the human UCP3 gene. In this instance, the entire coding region and 3' untranslated region was retrieved by the 838F and 3U3F primer combinantion. However, the skilled artisan, aided with this specification, will understand the more far reaching cDNA cloning process disclosed herein: multiple primer combinations from an EST or other partial cDNA sequence, in combination with flanking vector primer oligonucleotides may be used to "walk" in both directions away from the internal gene specific sequence and respective primers such that a contig representing a full length cDNA may be constructed. This procedure relies on the ability to screen multiple pools which comprise a repsentive portion of the total cDNA library. This procedure is not dependent upon using a cDNA library with directionally cloned inserts. Instead, both 5' and 3' vector and gene specific primers are added and a contig map is constructed from additional screening of positive pools using both vector primers and gene specific primers. Of course, these gene specific primers are intially constructed from a known nucleic acid fragment such as an expressed sequence tag. However, as the walk continues, gene specific primers are utilized from the 5' and 3' boundaries of the newly identified regions of the cDNA. As the walk continues, there is still no requirement that the vector orientation of a yet unidentified fragment be known. Instead, all combinations are tested on a positive pool and the actual vector orientation is determined by the ability of certain vector/gene specific primers to generate the predicted PCR fragment. A full-length cDNA may then be easily constructed by known subcloning procedures.

A variety of mammalian expression vectors may be used to express recombinant UCP3 in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

Commercially available mammalian expression vectors which may be suitable for recombinant UCP3 expression, include but are not limited to, pcDNA3.1 (Invitrogen), pBlueBacHis2 (Invitrogen), pLITMUS28, pLITMUS29, pLITMUS38 and pLITMUS39 (New England Bioloabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

A variety of bacterial expression vectors may be used to express recombinant UCP3 in bacterial cells. Commercially available bacterial expression vectors which may be suitable for recombinant UCP3 expression include, but are not limited to pCR2.1 (Invitrogen), pET11a (Novagen), lambda gt11 (Invitrogen), pcDNAII (Invitrogen), pKK223-3 (Pharmacia).

A variety of fungal cell expression vectors may be used to express recombinant UCP3 in fungal cells. Commercially available fungal cell expression vectors which may be suitable for recombinant UCP3 expression include but are not limited to pYES2 (Invitrogen), *Pichia* expression vector (Invitrogen).

A variety of insect cell expression vectors may be used to express recombinant receptor in insect cells. Commercially available insect cell expression vectors which may be suitable for recombinant expression of UCP3 include but are not limited to pBlueBacIII and pBlueBacHis2 (Invitrogen).

An expression vector containing DNA encoding a UCP3-like protein may be used for expression of UCP3 in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to *Drosophila* and silkworm derived cell lines. Cell lines derived from mammalian species which may be suitable and which are commercially available, include but are not limited to, L cells L–M(TK⁻) (ATCC CCL 1.3), L cells L–M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are individually analyzed to determine whether they produce UCP3 protein. Identification of UCP3 expressing cells may be done by several means, including but not limited to immunological reactivity with anti-UCP3 antibodies, and the presence of host cell-associated UCP3 activity.

The cloned UCP3 cDNA obtained through the methods described above may be recombinantly expressed by molecular cloning into an expression vector (such as pcDNA3.1, pCR2.1, pBlueBacHis2 and pLITMUS28) containing a suitable promoter and other appropriate transcription regulatory elements, and transferred into prokaryotic or eukaryotic host cells to produce recombinant UCP3. Techniques for such manipulations can be found described in Sambrook, et al., supra, are discussed at length in the Example section and are well known and easily available to the artisan of ordinary skill in the art.

Expression of UCP3 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the UCP3 cDNA sequence(s) that yields optimal levels of UCP3 protein, UCP3 cDNA molecules including but not limited to the following can be constructed: the full-length open reading frame of the UCP3 cDNA and various constructs containing portions of the cDNA encoding only specific domains of the protein or rearranged domains of the protein. All constructs can be designed to contain none, all or portions of the 5' and/or 3' untranslated region of UCP3. UCP3 activity and levels of protein expression can be determined following the introduction, both singly and in combination, of these constructs into appropriate host cells. Following determination of the UCP3 cDNA cassette yielding optimal expression in transient assays, this UCP3 cDNA construct is transferred to a variety of expression vectors (including recombinant viruses), including but not limited to those for mammalian cells, plant cells, insect cells, oocytes, bacteria, and yeast cells.

Levels of UCP3 protein in host cells is quantified by a variety of techniques including, but not limited to, immunoaffinity and/or ligand affinity techniques. UCP3-specific affinity beads or UCP3-specific antibodies are used to isolate $^{35}$S-methionine labeled or unlabelled UCP3 protein. Labeled UCP3 protein is analyzed by SDS-PAGE. Unlabelled UCP3 protein is detected by Western blotting, ELISA or RIA assays employing UCP3 specific antibodies.

Following expression of UCP3 in a host cell, UCP3 protein may be recovered to provide UCP3 in active form. Several UCP3 purification procedures are available and suitable for use. Recombinant UCP3 may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant UCP3 can be separated from other cellular proteins by use of an immuno-affinity column made with monoclonal or polyclonal antibodies specific for full length UCP3, or polypeptide fragments of UCP3. Additionally, polyclonal or monoclonal antibodies may be raised against a synthetic peptide (usually from about 9 to about 25 amino acids in length) from a portion of the protein as disclosed in SEQ ID NO:12. Monospecific antibodies to UCP3 are purified from mammalian antisera containing antibodies reactive against UCP3 or are prepared as monoclonal antibodies reactive with UCP3 using the technique of Kohler and Milstein (1975, *Nature* 256: 495–497). Monospecific antibody as used herein is defined as a single antibody species or multiple antibody species with homogenous binding characteristics for UCP3. Homogenous binding as used herein refers to the ability of the antibody species to bind to a specific antigen or epitope, such as those associated with the UCP3, as described above. UCP3 specific antibodies are raised by immunizing animals such as mice, rats, guinea pigs, rabbits, goats, horses and the like, with an appropriate concentration of UCP3 or UCP3 synthetic peptide either with or without an immune adjuvant.

Preimmune serum is collected prior to the first immunization. Each animal receives between about 0.1 mg and about 1000 mg of UCP3 associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the UCP3 protein or UCP3 synthetic peptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of UCP3 in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with UCP3 are prepared by immunizing inbred mice, preferably Balb/c, with UCP3. The mice are immunized by the IP or SC route with about 1 mg to about 100 mg, preferably about 10 mg, of UCP3 in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of UCP3 in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using UCP3 as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-UCP3 mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of UCP3 in body fluids or tissue and cell extracts.

It is readily apparent to those skilled in the art that the above described methods for producing monospecific antibodies may be utilized to produce antibodies specific for UCP3 polypeptide fragments, or full-length UCP3 polypeptide.

UCP3 antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing UCP3 or UCP3 fragments are slowly passed through the column. The column is then washed with phosphate buffered saline until the optical density ($A_{280}$) falls to background, then the protein is eluted with 0.23 M glycine-HCl (pH 2.6). The purified UCP3 protein is then dialyzed against phosphate buffered saline.

The novel UCP3 of the present invention is suitable for use in an assay procedure for the identification of compounds which modulate UCP3 activity. Modulating UCP3 activity, as described herein includes the inhibition or activation of the protein and also includes directly or indirectly affecting the cell cycle regulatory properties associated with UCP3 activity. Compounds which modulate UCP3 activity include agonists, antagonists, inhibitors, activators, and compounds which directly or indirectly affect regulation of the UCP3 activity and/or the UCP3 uncoupling activity.

The UCP3 of the present invention may be obtained from both native and recombinant sources for use in an assay procedure to identify UCP3 modulators. In general, an assay procedure to identify UCP3 modulators will contain the UCP3-protein of the present invention, and a test compound or sample which contains a putative UCP3 modulator. The test compounds or samples may be tested directly on, for example, purified UCP3 protein whether native or recombinant, subcellular fractions of UCP3-producing cells whether native or recombinant, and/or whole cells expressing the UCP3 whether native or recombinant. The test compound or sample may be added to the UCP3 in the presence or absence of a known UCP3 modulator. The modulating activity of the test compound or sample may be determined by, for example, analyzing the ability of the test compound or sample to bind to UCP3 protein, activate the protein, inhibit UCP3 activity, inhibit or enhance the binding of other compounds to the UCP3 protein, modifying receptor regulation, or modifying an intracellular activity.

Therefore, the present invention also relates to subcellular membrane fractions of the recombinant host cells (both prokaryotic and eukaryotic as well as both stably and transiently transformed cells) comprising the nucleic acids of the present invention. These subcellular membrane fractions will comprise UCP3 at levels substantially above wild type levels and hence will be useful in various assays described throuhgout this specification.

The identification of modulators of UCP3 activity will be useful in treating disease states involving, as an example but not a limitation, obesity and diabetes, by manipulating the interrelated process of balancing food intake, energy expenditure and glucose metabolism within the patient. Therefore, modulators to treat hyperactive conditions of energy expenditure which originate in the mitochondria of skeletal muscle will also be within the purview of the present invention.

The present invention is also directed to methods for screening for compounds which modulate the expression of DNA or RNA encoding a UCP3 protein of the present invention or which modulates the function of a such a UCP3 protein. Compounds which modulate these activities may be DNA, RNA, peptides, proteins, or non-proteinaceous organic molecules. Compounds may modulate by increasing or attenuating the expression of DNA or RNA encoding the UCP3 protein, or the function of a UCP3 protein. Compounds that modulate the expression of DNA or RNA encoding the UCP3 protein or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing modified UCP3, antibodies to UCP3, or modified UCP3 protein may be prepared by known methods for such uses.

The DNA molecules, RNA molecules, recombinant protein and antibodies of the present invention may be used to screen and measure levels of UCP3 DNA, RNA or protein. The recombinant proteins, DNA molecules, RNA molecules and antibodies lend themselves to the formulation of kits suitable for the detection and typing of UCP3. Such a kit would comprise a compartmentalized carrier suitable to hold in close confinement at least one container. The carrier would further comprise reagents such as recombinant UCP3 protein or anti-UCP3 antibodies suitable for detecting UCP3. The carrier may also contain a means for detection such as labeled antigen or enzyme substrates or the like.

Pharmaceutically useful compositions comprising modulators of UCP3 may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modified UCP3.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

By computer analysis of a genomic database, molecular cloning and DNA sequencing a novel member of the human UCP3 gene family has been identified. This new cDNA fragment encodes a novel human uncoupling protein which may be useful as a gene therapy vehicle or a drug target in such diseases as obesity and diabetes.

Northern hybridization experiments with RNA from various cell and tissues indicates that UCP3 is expressed in various human tissue, including skeletal muscle, brain, and heart, with predominant expression in skeletal muscle.

The following examples are provided as illustrative of the present invention without, however, limiting the same thereto.

EXAMPLE 1

Identification of Partial DNA Fragments Encoding Human UCP3

The nucleotide sequence for human UCP1 (Cassard et al., 1990, *J. Cell. Biochem.* 43: 255–264) is deposited in Genbank and is assigned accession number U28480. The nucleotide sequence for human UCP2 (Fleury et al., 1997, *Nature Genetics* 15: 269–272)) is deposited in Genbank and is assigned accession number U76367. The nucleotide sequences of UCP1 and UCP2 were used to search the Genbank EST sequences by Blastn (see Altschull et al., 1990, J. Mol. Biol. 215: 403–410). The Blastn search identified an expressed sequence tag (EST) detected among the Merck-Washington University EST's with accession number AA192136, which is:

The EST disclosed as SEQ ID NO:2 shows an open reading frame encoding a novel protein fragment showing homology to human UCP1 and human UCP2. SEQ ID NO:2 represents the 5' portion of the cDNA Image Clone No. 628529. The 3' sequence read of cDNA Image Clone No. 628529 has the accession number aa192553, which is as follows:

```
GGTGACCTACGACATCCTCAAGGAGAAGCTGCTGGACTACCACCTGCTCACTGACAACT (SEQ ID NO:1).

TCCCCTGCCACTTTGTCTCTGCCTTTGGAGCCGGCTTCTGTGCCACAGTGGTGGCATCC

CCGGTGGACGTGGTGAAGACCCGGTATATGAACTCACCTCCAGGCCAGTACTTCAGCCC

CCTCGACTGTATGATAAAGATGGTGGCCCAGGAGCGCCACCAGCCTTCTACAAGGGATT

TACACCCTCCTTTTTGCGTTTGGGATCCTGGAACGTGGTGATGTTCGTAACCTATGAGC

AGCTGAAACGGGCCCTGATGAAAGTCCAGATGTTACGGGAATCACCGTTTTGAACAAGA

CAAGAAGGCCACTGGTAGCTAACGTGTCCGAAACCAGTTAAGAATGGAAG
```

An "N" residue is added at base number 249 in order to preserve the open reading frame of this EST. This corrected version of AA192136 is as follows:

```
GGTGACCTACGACATCCTCAAGGAGAAGCTGCTGGACTACCACCTGCTCACTGACAACT (SEQ ID NO:2).

TCCCCTGCCACTTTGTCTCTGCCTTTGGAGCCGGCTTCTGTGCCACAGTGGTGGCATCC

CCGGTGGACGTGGTGAAGACCCGGTATATGAACTCACCTCCAGGCCAGTACTTCAGCCC

CCTCGACTGTATGATAAAGATGGTGGCCCAGGAGCGCCACCAGCCTTCTACAAGGGATT

TACACCCTCCTTNTTTGCGTTTGGGATCCTGGAACGTGGTGATGTTCGTAACCTATGAG

CAGCTGAAACGGGCCCTGATGAAAGTCCAGATGTTACGGGAATCACCGTTTTGAACAAG

ACAAGAAGGCCACTGGTAGCTAACGTGTCCGAAACCAGTTAAGAATGGAAG
```

SEQ ID NO:1 is a component of Stratagene® muscle cDNA library 937209 and is identified as cDNA Image Clone No. 628529. This Stratagene muscle cDNA library was generated by standard methods and cDNAs are cloned unidirectionally into EcoRI/XhoI digested pBS(SK⁻) plasmid. The mRNA for this library was isolated from the skeletal muscle of an adult human patient suffering from malignant hyperthermia. This cDNA clone is publically available by Genbank Accession No. AA192136, Image Clone ID No. 628529, and Washington University Clone ID No. zq02d09.r1. This construct is available from Research Genetics, Inc., 2130 Memorial Parkway SW, Hunstville, Ala. 35801 (http://www.resgen.com).

SEQ ID NO:1 was used as a query to search Genbank with Blastn. A second EST, with accession number Z28895 (and assigned Genbank number HSBB6C051) was identified and is disclosed throughout this specification as SEQ ID NO:3, which is:

```
CGAGCAGCTGAAACGGGCCCTGATGAAAGTCCAGATGTTACGGGNATCACCGTTTTGAA (SEQ ID NO:3).

CAAGACAAGAAGGCCACTGGTAGCTAACGTNTCCGAAACCAGTTAAGANTGGAAGAAAA

CGGTCCATCCACGNACACATGGACACAGACCCACACATNTT
```

```
TTTTTTTTGTTCTTACTCCCACACCTAAGGTGGAANTTCTTTTATTGAGTCATAATAAT  (SEQ ID NO:4).

TTCCCGAGAATTCCGAGTCCTGCTACTTTAGGTTCTTGCCCAGGAATCCACCTCTTTTC

CCCCAAGCCCAACAATCCTTTGAGGTACTCATGATTGAGCGCGTGGTGGGGGGGGTGG

GGAAGAGGCTGCATGGGGGTGGGGCTCCTGTGGCTTCACGTCATCCACTGTCACCTCTG

GTCCCCAAGTCTCTGGATCCTTTGGTCTCACCTCTAGACAACCGGCGGGGTTCAAACCT

TCTTCCCTGGCAACTCCTCTCTGTCCCGACAAAATCTCTCCCAAGGCATTGTCCTTGTA

GTTAGATTTACACAGAGCTTTTGCTTTTATAAAGTGCGTTCATGCCCAGCTTCTCACTT

GCATGTCATAGCACCCCTGGTGAGGTGGACAGGGAAGGGATGGCTCCCTCCATTTTGTA

GGAAAGTNGGGG
```

EXAMPLE 2

Isolation and Characterization of DNA Fragments Encoding Full-Length Human UCP3

The exemplified full length cDNA of the present invention was generated by a novel method of cDNA screening as described in the Detailed Description of the Invention.

The foregoing process is exemplifed for isolation and characterization of a full-length cDNA encoding human UCP3. Briefly, a random oligo dT primed fetal brain cDNA library consisting of approximately 4.0 million primary clones was constructed in the plasmid vector pBluescript (Stratagene, LaJolla, Calif.). The primary clones were subdivided into 188 pools with each pool containing approximately 20,000 clones. Each pool was amplified separately and the resulting plasmid pools were collected and transferred into two 96-well plates.

Primer pairs 5'-AAGCTGCTGGACTACCACCTGCTC-3' (F29; SEQ ID NO:5), 5'-TACTGGCCTGGAGGTGAGT-TCA-3' (R147: SEQ ID NO:6) as designed from AA192136; 5'-CCAAGCCCAACAATCCTTTGA-3' (3U3F; SEQ ID NO:7) and 5'-CCAAAGGATCCAGAGACTTGG-3' (3U3R; SEQ ID NO:8) as designed from AA192553, and pBluescript SK vector primers 838F (5'-TTGTGTGGAAT-TGTGAGCGGATAAC-3'; SEQ ID NO:9) and 578R (5'-CCAGGGTTTTCCCAGTCACGAC-3'; SEQ ID NO:10) were used to scan by PCR a human fetal brain cDNA library distributed in a 96-well plate separately. Both the F29/R147-838F/578R scan and the 3U3F/3U3R-838F/578R scans scored positive in pools D10, E10 and F2. Gene specific primer 3U3F (SEQ ID NO:8, the 5' oligonucleotide from the 3' EST (AA192553, SEQ ID NO:4) and pBluescript SK vector primer 838F SEQ ID NO:9) amplified a fragment of about 2.4 kb from both pool E10 and pool F2. The fragments from E10 and F2 were gel purified, mixed, subcloned into the vector pTA2.1 (Invitrogen, San Diego, Calif., USA) by TA cloning. Four positive clones, the original PCR fragment, as well the I.M.A.G.E. clone #628529 (SEQ ID NOS:1 and 2) were sequenced by primer walking. The sequences were then assembled into a contig of 2340 base pairs which is as set forth in SEQ ID NO:11 and shown in FIGS. 1A–1B. This sequence contains an open reading frame that encodes a polypeptide of 312 amino acids as set forth in SEQ ID NO:12 and shown in FIG. 2A–2D and FIG. 3.

EXAMPLE 3

Construction of a Yeast Expression Vector and Transformed Yeast Cell Line Expressing Human UPC3

A pair of primers, UCP3.-9F.RI20mer (5'CATAGAATTC-CAGGACTATGGTTGGAC3', SEQ ID NO:13), and UCP3.1308R.XhoI20mer (5'CATTCTCGAGCTAC-CAGTGGCCTTCTTG3', SEQ ID NO:14) were used to generate a PCR product of human UCP3 tagged with EcoRI and XhoI sites at the 5' and 3' ends, respectively, using pCR2.1-UCP3.1 as the template. The PCR product was digested with EcoRI and XhoI and purified from an agarose gel. This fragment was ligated into a yeast expression vector pYES2 (Invitrogen, San Diego, Calif.) that was also digested with EcoRI and XhoI such that UCP3 is under the control of S. cerevisiae GALL promoter. Multiple recombinants isolated after transformation into E. coli were picked and sequenced using three UCP3 internal primers in combinatition with two pYES2 vector primers (5'CCCG-GATCGGACTACTAGCA, (SEQ ID NO:15); 5'GGGGG-GAGGGCGTGAATGTAA; [SEQ ID NO:16]). Mutation-free clones of pYES2-UCP3 were then transformed into two Saccharomyces cerevisiae strains INVSc1 (MATa, his3D1, leu2, trp1-289, ura3-52) and YPH499(MATa, ura3-52, lys2-801, ade2-101,trp1-D63, his3-D200, leu2-D1) using lithium acetate method and selected on Sc-ura media. The expression of UCP3 was achieved by induction in Sc-ura media with 2% galactose and 3% glycerol.

The diploid Saccharomyces cerevisiae strain W303 (MATa/a, can1-100, ade2-10, his3-11,-15, leu2-2,-112, trp1-D1, ura3-1) was also used for the expression of UCP3. Human UCP3 was expressed under the control of GAL1 promoter in pYES2 (Invitrogen, San Diego, Calif.). Constructs were made directly in yeast using a gap repair strategy. The entire open reading frame of human UCP3 was amplified using a pair of primers that incorporated a yeast translation start site (ATAATG). Taq Additive (Stratagene, La Jolla, Calif.) was included in PCR reaction to enhance amplification fidelity. The PCR product was fused to GAL1 at the 5' end and to CYC1 terminator at the 3' end by co-transforming the PCR product and pYES2 followed by selection on Sc-Ura medium. More than 50% of the transformants contained the expected GAL1-UCP3 plasmids. Consistent results were obtained from multiple independent clones for growth and flow cytometry analysis. For the growth assay, the W303 strain containing the vector alone or UCP3 expression plasmid was streaked onto Sc-Ura media with 3% glycerol and 2% galactose and incubated at 30° C. for 48 hours. To measure mitochondria membrane potential, cells were grown in Sc-Ura media supplemented with raffinose. Galactose was added to induce the expression of UCP3 for five hours. Fluorescent probe DiOC6 (3,3'-dihexyloxacarbocyanine iodine) was added after cell concentration was adjusted to two millions per ml. Data were collected and analyzed as described (Bouillaud et al., 1994. *EMBO J.* 13: 1990–1997). A total 10,000 objects were taken for the histograms. For the display of fluorescence intensity, a three-order logarithmic scale was used.

Figure 8A:
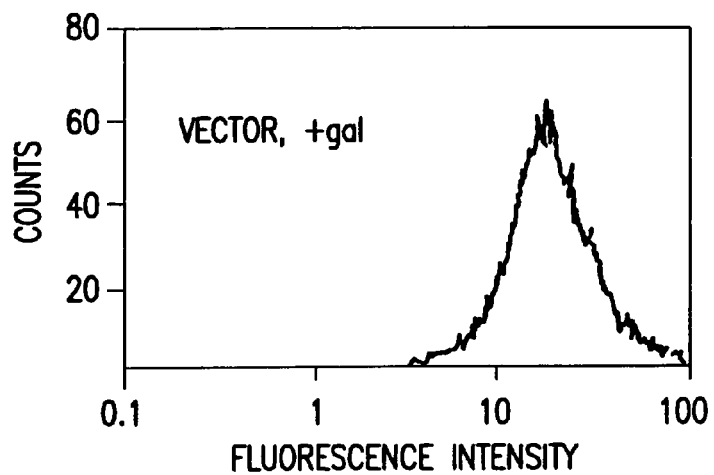
FIG. 8A, FIG. 8B and FIG. 8C show flow cytometry analysis of mitochondria membrane potential with UCP3 expression in yeast. The $S.\ cerevisiae$ strain W303 containing vector alone (FIG. 8A) or UCP3 expression plasmids (FIG. 8B and FIG. 8C) were stained with the potential sensitive dye, DiOC6 and analyzed by FACS. The X-axis represents the intensity of fluorescence on logarithmic scale while the Y-axis indicates the number of cells. "+gal" indicates that cells were induced with galactose for 5 hours. "–gal" indicates cells were maintained in raffinose media without the induction by galactose. A decrease in fluorescence intensity indicates a reduction in mitochondria membrane potential.
Figure 8B:
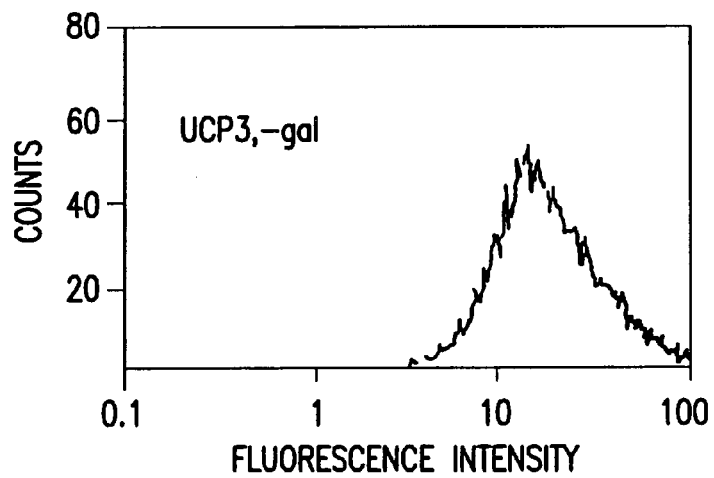
Figure 8C:
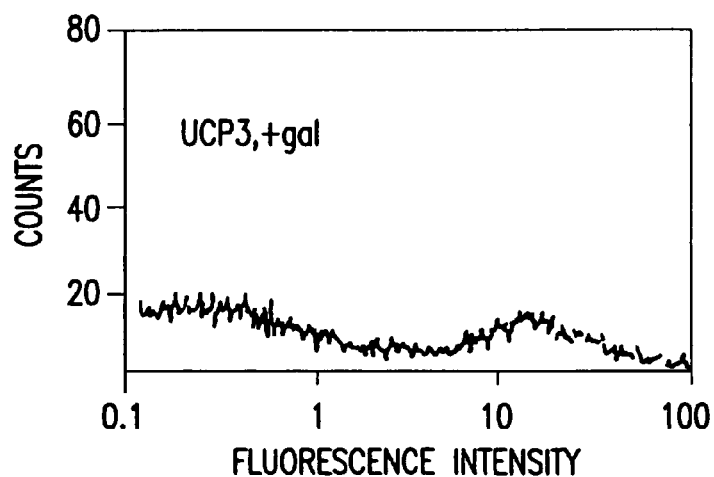

The biochemical activity of UCP1 and UCP2 have previously been studied by measuring the defects of aerobic growth in yeast expressing UCPs. To test that UCP3 encodes an uncoupling protein for mitochondria, UCP3 was expressed under the control of a tightly inducible promoter GALL in the yeast system as previously described for UCP1 and UCP2 (Fleury et al., 1997, *Nature Genetics* 15: 269–272; Gimeno et al., 1997, *Diabetes* 46, 900–906). Induction with galactose resulted in a significant decrease in the growth rate of strains containing UCP3 relative to cells with vector alone. To confirm more directly that UCP3 reduced the mitochondria membrane potential, the fluorescent intensity of cells labeled with the potential sensitive dye DiOC6 was measured using flow cytometry analysis. Induction of UCP3 expression by galactose significantly reduced the membrane potential of mitochondria compared with strains containing vector alone (FIGS. 8A and 8C). In addition, no membrane potential shift was observed when UCP3 expression was not induced (FIG. 8B). Two membrane potential peaks were observed after UCP3 induction (FIG. 8C). Similar results were observed for UCP2 (Fleury et al., 1997, *Nature Genetics* 15: 269–272). The most likely explanation for this observation is that one peak represents cells with reduced membrane potential due to expression of UCP3 while the other peak represents cells with normal membrane potential due to the loss of UCP3 expression. When UCP2 was cloned into the same vector as UCP3 and transformed into the same yeast strain, UCP2 reduced membrane potential to a greater extent compared with UCP2. The data indicate that UCP3 encodes an uncoupling protein that is able to decrease the membrane potential of mitochondria.

EXAMPLE 4

Tissue Distribution Of UCP3 Expression

Human multiple tissue Northern Blot #7760-1, Human Brain Northern Blot II #7755-1, Human Brain Northern Blot III #7750-1, and Human multiple tissue Northern Dot Blot were purchased from Clontech. The probe was made by PCR amplification of coding region of UCP3 (SEQ ID NO:11). This fragment was labeled with $^{32}$p and used to probe the Northern blot as described in the Clontech procedures, which are well known in the art. The blots were exposed to X-ray film with an intensifying screen at −70° C. for times as indicated in the figure. FIGS. 4A–4C is an autoradiograph which shows that UCP3 is highly expressed in skeletal muscle as a transcript of ~2.4 kb (FIGS. 4A & B). Two minor transcripts, ~6.0 kb and 7.5 kb are also expressed in skeletal muscle (FIG. 4A). In addtion, UCP3 is also weakly expressed as a transcript of ~2.4 kb in the heart. Probing with human beta-actin probe (FIG. 4C) shows that all the lanes have approximately equal amount of total polyA RNA, indicating that detection of UCP3 only in skeletal muscle and in the heart is not due to the lack of RNA in the other tissue lanes. Also, In the brain, ucp3 is most abundantly expressed in the corpus collosum as a transcript of ~2.4 kb.

The expression pattern of UCP3 appears to be unique, because it is abundantly and nearly exclusively expressed in skeletal muscle. Even though UCP3 expression was also detected in the heart and brain, it was found at much lower levels. Skeletal muscle is responsible for more than half of energy expenditure at resting stage. Differences in energy expenditure of skeletal muscle can explain most of the variation in basal metabolic rate between individuals (Ravussin and Bogardus, 1992, *Am J Clin Nutr* 55: 242S–245S). The proton leak was shown to account for around one-half of the resting respiration rate of perfused rat skeletal muscle (Rolfe and Brand, 1996, *Am J Physiol* 271: C1380–1389). Furthermore, free fatty acids-activated uncoupling in skeletal muscle was also observed previously (Brustovetsky et al., 1992, *FEBS Lett* 305: 15–17). Thus, UCP3 should provide a significant contribution to the uncoupling activities in skeletal muscle since it is much more strongly expressed than UCP1 and UCP2, and its activity is likely to be dependent on free fatty acids.

EXAMPLE 5

Characterization and Chromosomal Localization of Genes Encoding UCP3

To map the position of ucp3 in the human genome, the primer pair 3U3F (SEQ ID NO:7) and 3U3R (SEQ ID NO:8) of ucp3 was used to carry out PCR reactions with the 83 clones of the Stanford radiation hybrid panel (Cox et al., 1990, *Science,* 250:245:250). The PCR results were scored and submitted to the Stanford Genome Center for linkage analysis. It was found that ucp3 is located close to the marker D11S944e with a lod score of 9.4, which corresponds to the cytogenetic location of 11q13.1~11q23.3.

Radiation hybrid mapping placed this gene into a region around chromosome 11q21, the same region where ucp2 is located (Fleury et al., 1997, *Nature Genetics* 15: 269–272). Sequence analysis showed that UCP3 is 72% identical to UCP2 and 56% identical to UCP1 at the amino acid level. Hydropathy analysis showed that UCP3 has the same hydrophobicity/hydrophilicity profile as UCP1 and 2. Like UCP1 and UCP2, the UCP3 protein also consists of three repeating units with each unit containing 2 transmembrane domains. Given this homology to UCP1 and UCP2, human UCP3 is predicted to encode an uncoupling protein. Two mouse bacterial artificial chromosome (BAC) clones containing mouse UCP2 were obtained using an STS in the 3' UTR of mouse UCP2. After the mouse UCP3 sequence was determined, PCR with mouse UCP3-specific primers scored positive with both mouse UCP2 BAC clones. In the mouse, the UCP2 and UCP3 genes were found to be in the same BAC clone suggesting that UCP3 is located close to UCP2 on chromosome 7. Thus, UCP2 and UCP3 are located in the same chromosomal region in both human and mouse, while human UCP1 was mapped to 4q31. The chromosomal regions where UCP2 resides are linked to obesity and hyperinsulinemia in both human and mouse, and so UCP2 was hypothesized to be a candidate gene for these diseases (Taylor and Phillips, 1996, *Genomics* 34, 389–398; Fleury et al., 1997, *Nature Genetics* 15: 269–272). The close location of UCP3 to UCP2 suggests that UCP3 is also a candidate gene for obesity and hyperinsulinemia. In addition, the close homology and location between UCP2 and UCP3 suggested that the two genes arose from a gene duplication event after UCP1 was separated.

Alignment of the six protein sequences of UCP1 to UCP3 of human and mouse reveals a highly clustered pattern of the conserved residues. The transmembrane domains and their immediate following sequences are much more conserved than the sequences between the transmembrane domains. Moreover, each allbnb motif following the first transmembrane domain of each repeat unit is perfectly conserved among the six proteins. Thus, UCP3 is a typical member of the mitochondria transport protein superfamily. UCP1 activity is inhibited by nucleotides but activated by free fatty acids. Affinity labeling and site-directed mutagenesis demonstrated that the region between transmembrane domain 5 and 6 bound to nucleotides (Mayinger and Klingenberg, 1992, *Biochemistry* 31: 10536–10543; Winkler and Klingenberg, 1992, *Eur J Biochem* 203: 295–304). Particularly, deletion of the putative nucleotide binding motif (amino acid residue 261 to 269) renders UCP1 resistant to nucleotide-mediated inhibition (Bouillaud et al, 1994, *EMBO J.* 13, 1990–1997). Substitution of Phe 267 by a Tyr also results in higher uncoupling activity (Bouillaud et al., id.). Both UCP2 and UCP3 contain a Tyr instead of a Phe at this position, suggesting that UCP2 and UCP3 has higher basal activity. On the other hand, UCP1 and UCP3 both have a Thr at the position corresponding residue 264 of UCP1 whereas UCP2 has an Arg. The presence of a positively charged residue in this motif may imply a higher affinity of UCP2 for nucleotides and, consequently, increased sensitivity to nucleotide-mediated inhibition. The very C-terminus of UCP1 was shown to be important for activation by fatty acids (Gonzalez-Barroso et al., 1996, *Eur J Biochem* 239: 445–450). Sequence alignments of the three UCP members, surprisingly, found that last 10 residues are not well conserved among each other at all, suggesting the activity of each UCP has different sensitivity to free fatty acids. In UCP1, change of Cys 304 to an Ala results in decreased activation while change to a Ser leads to increased activation by fatty acids (Gonzalez-Barroso et al., id.). Interestingly, UCP2 contains an Ala whereas UCP3 contains a Ser at the Cys 304 position, suggesting UCP3 has higher activity than UCP2. These comparisons suggest that UCP3 would be the most active among the three since UCP2 was shown to be more active than UCP1 under the same conditions (Fleury et al., 1997, *Nature Genetics* 15: 269–272; Gimeno et al., 1997, *Diabetes* 46: 900–906). In fact, expression of UCP3 in yeast reduced membrane potential more than UCP2.

EXAMPLE 6

Adenovirus-Mediated Leptin Expression

All animal experiments were carried out in accordance with our institutional guidance. A total of 10 age-match female ob/ob mice were weighed and injected through tail vein (IV) as follows: three with E1-deleted replication deficient adenoviral vector expressing leptin (Ad-leptin), three with helper-dependent adenoviral vector expressing leptin (HD-leptin), two with β-gal-expressing adenoviral vector (Ad-β-gal), and two were injected with buffer alone. The animals were then monitored for weight on a daily basis and sacrificed after one week of observation. Blood was collected for each animal and serum leptin levels were determined by Linco Research Inc. (St. Charles, Mo.) using an RIA assay. Total RNA was isolated from skeletal muscle tissue of each animal and used to prepare Northern blots. Approximately equal amounts of total RNA were loaded for each sample as estimated from the amount of ribosomal RNA in each lane. The blots were probed with human UCP3 and signals were quantified by phosphoimaging analysis (Molecular Dynamics, Sunnyvale, Calif.).

Figure 9A:
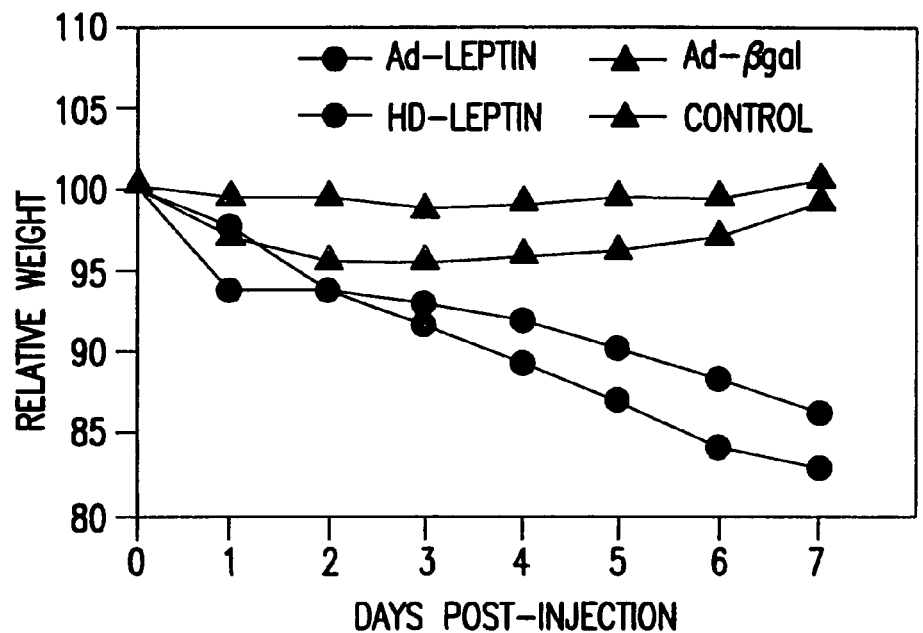
FIG. 9A and FIG. 9B shows the response of UCP3 expression to adenovirus-mediated leptin treatment.
Figure 9B:
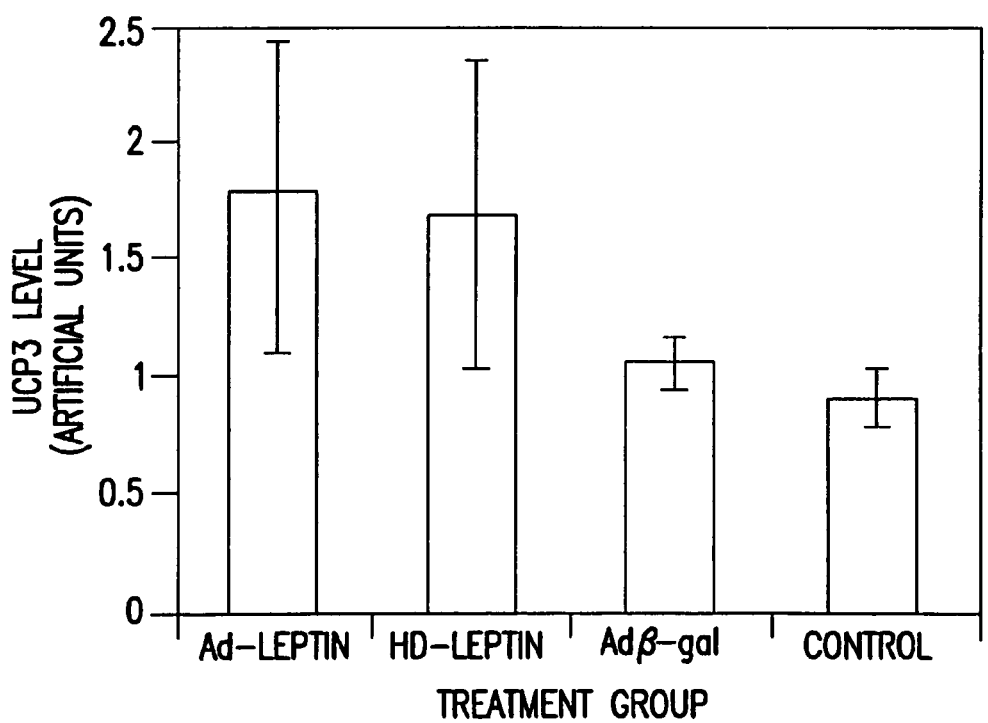

It has been reported that adenovirus-mediated leptin expression leads to significant reduction of body weight in ob/ob mice. Given the abundance of UCP3 in skeletal muscle, the effect of leptin treatment on UCP3 expression in skeletal muscle was tested by injecting adenoviruses expressing leptin into ob/ob mice and examining UCP3 expression after one week. Injection of adenoviruses expressing leptin, either helper-dependent (HD-leptin) or first generation (Ad-leptin), led to significant weight loss (approximately 15%) after one week while injection of adenoviral vector expressing b-galactosidase (Adb-gal) had no significant effect on body weight (FIG. 9A). Measurement of serum leptin levels at the end of one week confirmed high levels of leptin production in mice injected with HD-leptin (26.7±10 ng/ml) or Ad-leptin (21.8±16.7 ng/ml) but not in mice injected with Adb-gal (1.56±0.05 ng/ml) or buffer alone (2±0.17 ng/ml). Wild type lean mice have leptin levels at approximately 4.5 ng/ml. UCP3 levels were then checked in skeletal muscle of these animals. Mice treated with adenovectors expressing leptin, either Ad-leptin or HD-leptin, showed approximately an increase of 80% and 70%, respectively, in UCP3 RNA level (FIG. 9B, p=0.2 vs. buffer-injected mice). In contrast, mice treated with Adb-gal did not show significant change in UCP3 expression. If the average UCP3 level of animals showing weight loss (leptin-treated, n=6) was compared with that of animals showing no weight loss (b-galactosidase treated or untreated, n=4), the increase in UCP3 expression after leptin treatment was statistically significant (p=0.01). Thus, leptin treatment leads to increased UCP3 expression in skeletal muscle in ob/ob mice.

Leptin plays a pivotal role in the regulation of food intake and energy expenditure. Leptin-deficient ob/ob mice are hyperphagic and hypometabolic, and leptin treatment led to decreased food intake and increased metabolic rate (Halaas et al., 1995, *Science* 269: 543–546, Hwa et al., 1997, *Am J Physiol* 272, R1204–1209; Hwa et al., 1996 *Horm Metab Res* :28: 659–663). These results suggest that UCP3 may be involved in the increase of metabolic rate post-leptin treatment. Leptin treatment led to increased expression of UCP2 in pancreatic islets and adipose tissue (Zhou et al., 1997). Thus, both UCP2 and UCP3 are likely to be involved in the increase of metabolic rate post-leptin treatment.

EXAMPLE 7

Isolation and Characterization of DNA Fragments Encoding Full-Length Mouse UCP3

Mouse UCP3 was isolated by semi-nested PCR followed by 5' and 3' race. Three degenerate PCR primers were designed based on the conserved regions of the three uncoupling proteins: F441, 5'-CCNCTGGAYACNGCYAA-3' (SEQ ID NO:19); F755, 5'-CAGCCCACNGANGTNGT-3' (SEQ ID NO:20); and R1055, 5'-TTCACCACRTCNAC-NGG-3' (SEQ ID NO:21). First round PCR was carried out on mouse skeletal muscle cDNA with the primer pair F441+R1055. Second round PCR was carried out with the primer pair F755+R1055. All PCR reactions were carried out using AmpliTaq Gold (Perkin Elmer, NJ). The degerate PCR product was cloned into the vector pCR2.1 (Invitrogen, CA) and sequenced. Analysis of the sequences identified a partial cDNA sequence that was highly homologous to human UCP3. This partial sequence were then used to isolate the full-length sequence of mouse UCP3 by 5' and 3' race using a Marathon race kit from Clontech (Clontech Laboratories, CA). DNA sequences were all determined using the ABI Prism dye terminator system on ABI 377 machines. The full length cDNA encoding mouse UCP3 (SEQ ID NO:17) is shown in FIGS. 6A and 6B and the amino acid sequence of mouse UCP3 (SEQ ID NO:18) is shown in FIG. 7.

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
       (A) LENGTH: 404 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:1:

```
GGTGACCTAC GACATCCTCA AGGAGAAGCT GCTGGACTAC CACCTGCTCA CTGACAACTT      60

CCCCTGCCAC TTTGTCTCTG CCTTTGGAGC CGGCTTCTGT GCCACAGTGG TGGCATCCCC     120

GGTGGACGTG GTGAAGACCC GGTATATGAA CTCACCTCCA GGCCAGTACT TCAGCCCCCT     180

CGACTGTATG ATAAAGATGG TGGCCCAGGA GCGCCACCAG CCTTCTACAA GGGATTTACA     240

CCCTCCTTTT TGCGTTTGGG ATCCTGGAAC GTGGTGATGT TCGTAACCTA TGAGCAGCTG     300

AAACGGGCCC TGATGAAAGT CCAGATGTTA CGGGAATCAC CGTTTTGAAC AAGACAAGAA     360

GGCCACTGGT AGCTAACGTG TCCGAAACCA GTTAAGAATG GAAG                     404
```

(2) INFORMATION FOR SEQ ID NO:2:

(i) SEQUENCE CHARACTERISTICS:
       (A) LENGTH: 405 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:2:

```
GGTGACCTAC GACATCCTCA AGGAGAAGCT GCTGGACTAC CACCTGCTCA CTGACAACTT      60

CCCCTGCCAC TTTGTCTCTG CCTTTGGAGC CGGCTTCTGT GCCACAGTGG TGGCATCCCC     120

GGTGGACGTG GTGAAGACCC GGTATATGAA CTCACCTCCA GGCCAGTACT TCAGCCCCCT     180

CGACTGTATG ATAAAGATGG TGGCCCAGGA GCGCCACCAG CCTTCTACAA GGGATTTACA     240

CCCTCCTTNT TTGCGTTTGG GATCCTGGAA CGTGGTGATG TTCGTAACCT ATGAGCAGCT     300

GAAACGGGCC CTGATGAAAG TCCAGATGTT ACGGGAATCA CCGTTTTGAA CAAGACAAGA     360

AGGCCACTGG TAGCTAACGT GTCCGAAACC AGTTAAGAAT GGAAG                    405
```

(2) INFORMATION FOR SEQ ID NO:3:

(i) SEQUENCE CHARACTERISTICS:
       (A) LENGTH: 159 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:3:

CGAGCAGCTG AAACGGGCCC TGATGAAAGT CCAGATGTTA CGGGNATCAC CGTTTTGAAC    60

AAGACAAGAA GGCCACTGGT AGCTAACGTN TCCGAAACCA GTTAAGATTG GAAGAAAACG   120

GTCCATCCAC GNACACATGG ACACAGACCC ACACATNTT                         159

(2) INFORMATION FOR SEQ ID NO:4:

(i) SEQUENCE CHARACTERISTICS:
        (A) LENGTH: 484 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

TTTTTTTTGT TCTTACTCCC ACACCTAAGG TGGAANTTCT TTTATTGAGT CATAATAATT    60

TCCCGAGAAT TCCGAGTCCT GCTACTTTAG GTTCTTGCCC AGGAATCCAC CTCTTTTCCC   120

CCAAGCCCAA CAATCCTTTG AGGTACTCAT GATTGAGCGC GTGGTGGGGG GGGGTGGGGA   180

AGAGGCTGCA TGGGGTGGG GCTCCTGTGG CTTCACGTCA TCCACTGTCA CCTCTGGTCC   240

CCAAGTCTCT GGATCCTTTG GTCTCACCTC TAGACAACCG GCGGGGTTCA AACCTTCTTC   300

CCTGGCAACT CCTCTCTGTC CCGACAAAAT CTCTCCCAAG GCATTGTCCT TGTAGTTAGA   360

TTTACACAGA GCTTTTGCTT TTATAAAGTG CGTTCATGCC CAGCTTCTCA CTTGCATGTC   420

ATAGCACCCC TGGTGAGGTG GACAGGGAAG GGATGGCTCC CTCCATTTTG TAGGAAAGTN   480

GGGG                                                               484

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

AAGCTGCTGG ACTACCACCT GCTC                                          24

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:6:

TACTGCCCTG GAGGTGAGTT CA                                            22

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:7:

CCAAGCCCAA CAATCCTTTG A                                              21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:8:

CCAAAGGATC CAGAGACTTG G                                              21

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:9:

TTGTGTGGAA TTGTGAGCGG ATAAC                                          25

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:10:

CCAGGGTTTT CCCAGTCACG AC                                             22

(2) INFORMATION FOR SEQ ID NO:11:

(i) SEQUENCE CHARACTERISTICS:
        (A) LENGTH: 2340 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

TCGAACTCAC TCACCTCCCC TCTCACCTCA CTGCCCTCAC CAGCCAGCCT CTTGTCAAGT      60

GATCAGGCTG TCAACCAACT TCTCTAGGAT AAGGTTTCAG GTCAGCCTGT GTGTATAAGA     120

CCAGTGCCAA GCCAGAAGCA GCAGAGACAA CAGTGAATGA CAAGGAGGGG CCATCCAATC     180

CCTGCTGCCA CCTCCTGGGA TGGAGCCCTA GGGAGCCCCT GTGCTGCCCC TGCCGTGGCA     240

GGACTCACAG CCCCACCGCT GCACTGAAGC CCAGGGCTGT GGAGCAGCTC TCTCCTTGGA     300

```
CTCCTCTCGG CCCTAAAGGG ACTGGGCAGA GCCTTCCAGG ACTATGGTTG GACTGAAGCC      360

TTCAGACGTG CCTCCCACCA TGGCTGTGAA GTTCCTGGGG GCAGGCACAG CAGCCTGTTT      420

TGCTGACCTC GTTACCTTTC CACTGGACAC AGCCAAGGTC CGCCTGCAGA TCCAGGGGGA      480

GAACCAGGCG GTCCAGACGG CCCGGCTCGT GCAGTACCGT GGCGTGCTGG GCACCATCCT      540

GACCATGGTG CGGACTGAGG GTCCCTGCAG CCCCTACAAT GGGCTGGTGG CCGGCCTGCA      600

GCGCCAGATG AGCTTCGCCT CCATCCGCAT CGGCCTTTAC GACTCCGTCA AGCAGGTGTA      660

CACCCCCAAA GGCGCGGACA ACTCCAGCCT CACTACCCGG ATTTTGGCCG GCTGCACCAC      720

AGGAGCCATG GCGGTGACCT GTGCCCAGCC CACAGATGTG GTGAAGGTCC GATTTCAGGC      780

CAGCATACAC CTCGGGCCAT CCAGGAGCGA CAGAAAATAC AGCGGGACTA TGGACGCCTA      840

CAGAACCATC GCCAGGGAGG AAGGAGTCAG GGGCCTGTGG AAAGGAACTT TGCCCAACAT      900

CATGAGGAAT GCTATCGTCA ACTGTGCTGA GGTGGTGACC TACGACATCC TCAAGGAGAA      960

GCTGCTGGAC TATCACCTGC TCACTGACAA CTTCCCCTGC CACTTTGTCT CTGCCTTTGG     1020

AGCCGGCTTC TGTGCCACAG TGGTGGCCTC CCCGGTGGAC GTGGTGAAGA CCCGGTATAT     1080

GAACTCACCT CCAGGCCAGT ACTTCAGCCC CCTCGACTGT ATGATAAAGA TGGTGGCCCA     1140

GGAGGGCCCC ACAGCCTTCT ACAAGGGATT TACACCCTCC TTTTTGCGTT TGGGATCCTG     1200

GAACGTGGTG ATGTTCGTAA CCTATGAGCA GCTGAAACGG GCCCTGATGA AGTCCAGAT     1260

GTTACGGGAA TCACCGTTTT GAACAAGACA AGAAGGCCAC TGGTAGCTAA CGTGTCCGAA     1320

ACCAGTTAAG AATGGAAGAA AACGGTGCAT CCACGCACAC ATGGACACAG ACCCACACAT     1380

GTTTACAGAA CTGTTGTTTA CTTGTTGCTG ATTCAAGAAA CAGAAGTAGA AGAGAGAGGA     1440

TTCTGGTCTT CACTGCCATG CCTCAAGAAC ACCTTTGTTT TGCACTGACA AGATGGAAAA     1500

TAAATTATAT TAATTTTTGA AACCCATTAG GCATGCCTAA TATTTAGGCA AGAGAAAATA     1560

AACCAAGATA GATCCATTTG GACAAAATGG AAGGTTGGAG ACGTGTATCC CCGTGAAATC     1620

TGGTCAGATA ATGAATGATA AGCAGGAAGG ATGGCAAGCA CGGGACAGGA GGGGCCCACA     1680

ATGGAGTGGG AGATCAGCCA CGGAGCCTGG AGGGACGCCA CCCAGCAACA CAGAGCTGGC     1740

GACTGCAGCT GCACCATCAC ACATGCATCA TCAGCCTATT TGTAATATGT CTGCCACAGA     1800

GAGTCCTTTG GGATTCTAGG AAACCCAAGG AACAAGAGAA AAAACTAGAG CCTGTGCTAA     1860

AGAAGCCTGC TGGGCCCATG TGAGGCTGGG GTCGTAAATA TTCCCCGACG ACACTGAAGA     1920

ATCAAGAGGG CAGCCCCCAC TTCTCCTACA AAATGGAGGG AGCCATCCCT TCCCTGTCCA     1980

CCTCACCAGG GGTGCTATGA CATGCAAGTG AGAAGCTGGG CATGAACGCA CTTTATAAAA     2040

GCAAAAGCTC TGTGTAAATC TAACTACAAG GACAATGCCT TGGGAGAGAT TTTGTCGGGA     2100

CAGAGAGGAG TTGCCAGGGA AGAAGGTTTG AAAGATACGG TTGTCTAGAG GTGAGACCAA     2160

AGGATCCAGA GACTTGGGGA CCAGAGGTGA CAGTGGATGA CGTGAAGCCA CAGGAGCCCC     2220

ACCCCCATGC AGCTTTTTCC CCACCCCCCC CACCACGCGC TCAATCATGA GTACCTCAAA     2280

GGATTGTTGG GCTTGGGGGA AAAGAGGTGG ATTCCTGGGC AAGAACCTAA AGTAGCAGGA     2340
```

(2) INFORMATION FOR SEQ ID NO:12:

(i) SEQUENCE CHARACTERISTICS:
        (A) LENGTH: 312 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Val Gly Leu Lys Pro Ser Asp Val Pro Thr Met Ala Val Lys
1               5                   10                  15

Phe Leu Gly Ala Gly Thr Ala Ala Cys Phe Ala Asp Leu Val Thr Phe
                20                  25                  30

Pro Leu Asp Thr Ala Lys Val Arg Leu Gln Ile Gln Gly Glu Asn Gln
                35                  40                  45

Ala Val Gln Thr Ala Arg Leu Val Gln Tyr Arg Gly Val Leu Gly Thr
    50                  55                  60

Ile Leu Thr Met Val Arg Thr Glu Gly Pro Cys Ser Pro Tyr Asn Gly
65              70                  75                  80

Leu Val Ala Gly Leu Gln Arg Gln Met Ser Phe Ala Ser Ile Arg Ile
                85                  90                  95

Gly Leu Tyr Asp Ser Val Lys Gln Val Tyr Thr Pro Lys Gly Ala Asp
                100                 105                 110

Asn Ser Ser Leu Thr Thr Arg Ile Leu Ala Gly Cys Thr Thr Gly Ala
            115                 120                 125

Met Ala Val Thr Cys Ala Gln Pro Thr Asp Val Val Lys Val Arg Phe
130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
            180                 185                 190

Asn Cys Ala Glu Val Val Thr Tyr Asp Ile Leu Lys Glu Lys Leu Leu
            195                 200                 205

Asp Tyr His Leu Leu Thr Asp Asn Phe Pro Cys His Phe Val Ser Ala
    210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
                260                 265                 270

Tyr Lys Gly Phe Thr Pro Ser Phe Leu Arg Leu Gly Ser Trp Asn Val
            275                 280                 285

Val Met Phe Val Thr Tyr Glu Gln Leu Lys Arg Ala Leu Met Lys Val
        290                 295                 300

Gln Met Leu Arg Glu Ser Pro Phe
305                 310
```

(2) INFORMATION FOR SEQ ID NO:13:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:13:

CATAGAATTC CAGGACTATG GTTGGAC                    27

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:14:

```
CATTCTCGAG CTACCAGTGG CCTTCTTG                                       28
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:15:

```
CCCGGATCGG ACTACTAGCA                                                20
```

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:16:

```
GGGGGGAGGG CGTGAATGTA A                                              21
```

(2) INFORMATION FOR SEQ ID NO:17:

(i) SEQUENCE CHARACTERISTICS:
        (A) LENGTH: 1658 base pairs
        (B) TYPE: nucleic acid
        (C) STRANDEDNESS: double
        (D) TOPOLOGY: both (ii) MOLECULE TYPE: cDNA (xi) SEQUENCE DESCRIPTION: SEQ ID NO:17:

```
CCAGGAACAG CAGAGACAAC AGTGAATGGT GAGGCCCGGC CGTCAGATCC TGCTGCTACC     60

TAATGGAGTG GATCCTTAGG GTGGCCCTGC ACTACCCAAC CTTGGCTAGA CGCACAGCTT    120

CCTCCCTGAA CTGAAGCAAA AGATTGCCAG GCAAGCTCTC TCCTCGGACC TCCATAGGCA    180

GCAAAGGAAC CAGGCCCATT CCCCGGGACC ATGGTTGGAC TTCAGCCCTC CGAAGTGCCT    240

CCCACAACGG TTGTGAAGTT CCTGGGGGCC GGCACTGCGG CCTGTTTTGC GGACCTCCTC    300

ACTTTTCCCC TGGACACCGC CAAGGTCCGT CTGCAGATCC AAGGGGAGAA CCCAGGGGCT    360

CAGAGCGTGC AGTACCGCGG TGTGCTGGGT ACCATCCTGA CTATGGTGCG CACAGAGGGT    420

CCCCGCAGCC CCTACAGCGG ACTGGTCGCT GGCCTGCACC GCCAGATGAG TTTTGCCTCC    480

ATTCGAATTG GCCTCTACGA CTCTGTCAAG CAGTTCTACA CCCCCAAGGG AGCGGACCAC    540

TCCAGCGTCG CCATCAGGAT TCTGGCAGGC TGCACGACAG GAGCCATGGC AGTGACCTGC    600
```

-continued

```
GCCCAGCCCA CGGATGTGGT GAAGGTCCGA TTTCAAGCCA TGATACGCCT GGGAACTGGA      660

GGAGAGAGGA AATACAGAGG GACTATGGAT GCCTACAGAA CCATCGCCAG GGAGGAAGGA      720

GTCAGGGGCC TGTGGAAAGG GACTTGGCCC AACATCACAA GAAATGCCAT TGTCAACTGT      780

GCTGAGATGG TGACCTACGA CATCATCAAG GAGAAGTTGC TGGAGTCTCA CCTGTTTACT      840

GACAACTTCC CCTGTCACTT TGTCTCTGCC TTTGGAGCTG GCTTCTGTGC CACAGTGGTG      900

GCCTCCCCGG TGGATGTGGT AAAGACCCGA TACATGAACG CTCCCCTAGG CAGGTACCGC      960

AGCCCTCTGC ACTGTATGCT GAAGATGGTG GCTCAGGAGG GACCCACGGC CTTCTACAAA     1020

GGATTTGTGC CCTCCTTTCT GCGTCTGGGA GCTTGGAACG TGATGATGTT TGTAACATAT     1080

GAGCAACTGA AGAGGGCCTT AATGAAAGTC CAGGTACTGC GGGAATCTCC GTTTTGAACA     1140

AGGCAAGCAG GCTGCCTGGA ACAGAACAAA GCGTCTCTGC CCTGGGGACA CAGGCCCACA     1200

CGGTCCAGAA CCCTGCACTG CTGCTGACAC GAGAAACTGA ACTAAAAGAG GAGAGTTTTA     1260

GTCCTCCGTG TTTCGTCCTA AAACACCTCT GTTTTGCACT GACCTGATGG GAAATAAATT     1320

ATATTAATTT TTAAACCCTT TCCGGTTGGA TGCCTAACAT TTAGGCAAGA GACAACAAAG     1380

AAAACCAGAG TCAACTCCCT TGAAATGTAG GAATAAAGGA TGCATAATAA ACAGGAAAGG     1440

CACAGGTTTT GAGAAGATCA GCCCACAGTG TTGTCCTTGA ATCAAACAAA ATGGTCGGAG     1500

GAACCCTTCG GGTTCAGCAC AAAGAGGTGA CTACAGCCTT TTGGTCACCA GATGACTCCG     1560

CCCCTTTGTA ATGAGTCTGC CAAGTAGACT CTATCAAGAT TCTGGGGAAA GGAGAAAGAA     1620

CACATTGACC TGCCCGGGCG GCCGCTCGAG CCCTATGA                             1658
```

(2) INFORMATION FOR SEQ ID NO:18:

(i) SEQUENCE CHARACTERISTICS:
        (A) LENGTH: 308 amino acids
        (B) TYPE: amino acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:18:

```
Met Val Gly Leu Gln Pro Ser Glu Val Pro Pro Thr Thr Val Val Lys
1               5                   10                  15

Phe Leu Gly Ala Gly Thr Ala Ala Cys Phe Ala Asp Leu Leu Thr Phe
            20                  25                  30

Pro Leu Asp Thr Ala Lys Val Arg Leu Gln Ile Gln Gly Glu Asn Pro
        35                  40                  45

Gly Ala Gln Ser Val Gln Tyr Arg Gly Val Leu Gly Thr Ile Leu Thr
    50                  55                  60

Met Val Arg Thr Glu Gly Pro Arg Ser Pro Tyr Ser Gly Leu Val Ala
65                  70                  75                  80

Gly Leu His Arg Gln Met Ser Phe Ala Ser Ile Arg Ile Gly Leu Tyr
            85                  90                  95

Asp Ser Val Lys Gln Phe Tyr Thr Pro Lys Gly Ala Asp His Ser Ser
            100                 105                 110

Val Ala Ile Arg Ile Leu Ala Gly Cys Thr Thr Gly Ala Met Ala Val
        115                 120                 125

Thr Cys Ala Gln Pro Thr Asp Val Val Lys Val Arg Phe Gln Ala Met
    130                 135                 140
```

```
Ile Arg Leu Gly Thr Gly Gly Glu Arg Lys Tyr Arg Gly Thr Met Asp
145                 150                 155                 160

Ala Tyr Arg Thr Ile Ala Arg Glu Glu Gly Val Arg Gly Leu Trp Lys
                165                 170                 175

Gly Thr Trp Pro Asn Ile Thr Arg Asn Ala Ile Val Asn Cys Ala Glu
            180                 185                 190

Met Val Thr Tyr Asp Ile Ile Lys Glu Lys Leu Leu Glu Ser His Leu
        195                 200                 205

Phe Thr Asp Asn Phe Pro Cys His Phe Val Ser Ala Phe Gly Ala Gly
    210                 215                 220

Phe Cys Ala Thr Val Val Ala Ser Pro Val Asp Val Val Lys Thr Arg
225                 230                 235                 240

Tyr Met Asn Ala Pro Leu Gly Arg Tyr Arg Ser Pro Leu His Cys Met
                245                 250                 255

Leu Lys Met Val Ala Gln Glu Gly Pro Thr Ala Phe Tyr Lys Gly Phe
            260                 265                 270

Val Pro Ser Phe Leu Arg Leu Gly Ala Trp Asn Val Met Met Phe Val
        275                 280                 285

Thr Tyr Glu Gln Leu Lys Arg Ala Leu Met Lys Val Gln Val Leu Arg
    290                 295                 300

Glu Ser Pro Phe
305

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "degenerate oligonucleotide"

(xi) SEQUENCE DESCRIPTION: SEQ ID NO:19:

CCNCTGGAYA CNGCYAA                                                    17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "degenerate oligonucleotide"

(xi) SEQUENCE DESCRIPTION: SEQ ID NO:20:

CAGCCCACNG ANGTNGT                                                    17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: other nucleic acid
    (A) DESCRIPTION: /desc = "degenerate oligonucleotide"

(xi) SEQUENCE DESCRIPTION: SEQ ID NO:21:

TTCACCACRT CNACNGG                                                            17

What is claimed is:

1. A purified DNA molecule encoding human uncoupling protein 3 wherein said DNA molecule encodes a protein comprising the amino acid sequence as set forth in SEQ ID NO:12.

2. A purified DNA molecule encoding a human uncoupling protein 3 which comprises the nucleotide sequence as set forth in SEQ ID NO:11.

3. A DNA molecule of claim 2 which comprises from about nucleotide 344 to about nucleotide 1282 of SEQ ID NO:11.

4. An expression vector for the expression of a human uncoupling 3 protein in a recombinant host cell wherein said expression vector comprises the DNA molecule of claim 2.

5. An expression vector of claim 4 which is a eukaryotic expression vector.

6. An expression vector of claim 4 which is a prokaryotic expression vector.

7. A host cell which expresses a recombinant human uncoupling 3 protein wherein said host cell contains the expression vector of claim 4.

8. A host cell which expresses a recombinant human uncoupling 3 protein wherein said host cell contains the expression vector of claim 5.

9. A host cell which expresses a recombinant human uncoupling protein 3 wherein said host cell contains the expression vector of claim 6.

10. A process for the expression of a human uncoupling protein 3 in a recombinant host cell, comprising:
    (a) transfecting the expression vector of claim 4 into a suitable host cell;
    (b) culturing the host cells of step (a) under conditions which allow expression of the human uncoupling protein 3 from the expression vector; and,
    (c) isolating the human uncoupling protein 3 away from the host cells of step (b).

11. A purified DNA molecule encoding a human uncoupling protein 3 wherein said DNA molecule encodes a protein consisting of the amino acid sequence as set forth in SEQ ID NO:12.

12. A purified DNA molecule encoding human uncoupling protein 3 which consists of the nucleotide sequence

```
TCGAACTCAC TCACCTCCCC TCTCACCTCA CTGCCCTCAC CAGCCAGCCT

CTTGTCAAGT GATCAGGCTG TCAACCAACT TCTCTAGGAT AAGGTTTCAG

GTCAGCCTGT GTGTATAAGA CCAGTGCCAA GCCAGAAGCA GCAGAGACAA

CAGTGAATGA CAAGGAGGGG CCATCCAATC CCTGCTGCCA CCTCCTGGGA

TGGAGCCCTA GGGAGCCCCT GTGCTGCCCC TGCCGTGGCA GGACTCACAG

CCCCACCGCT GCACTGAAGC CCAGGGCTGT GGAGCAGCTC TCTCCTTGGA

CTCCTCTCGG CCCTAAAGGG ACTGGGCAGA GCCTTCCAGG ACTATGGTTG

GACTGAAGCC TTCAGACGTG CCTCCCACCA TGGCTGTGAA GTTCCTGGGG

GCAGGCACAG CAGCCTGTTT TGCTGACCTC GTTACCTTTC CACTGGACAC

AGCCAAGGTC CGCCTGCAGA TCCAGGGGGA GAACCAGGCG GTCCAGACGG

CCCGGCTCGT GCAGTACCGT GGCGTGCTGG GCACCATCCT GACCATGGTG

CGGACTGAGG GTCCCTGCAG CCCCTACAAT GGGCTGGTGG CCGGCCTGCA

GCGCCAGATG AGCTTCGCCT CCATCCGCAT CGGCCTTTAC GACTCCGTCA

AGCAGGTGTA CACCCCCAAA GGCGCGGACA ACTCCAGCCT CACTACCCGG

ATTTTGGCCG GCTGCACCAC AGGAGCCATG GCGGTGACCT GTGCCCAGCC

CACAGATGTG GTGAAGGTCC GATTTCAGGC CAGCATACAC CTCGGGCCAT

CCAGGAGCGA CAGAAAATAC AGCGGGACTA TGGACGCCTA CAGAACCATC

GCCAGGGAGG AAGGAGTCAG GGGCCTGTGG AAAGGAACTT TGCCCAACAT

CATGAGGAAT GCTATCGTCA ACTGTGCTGA GGTGGTGACC TACGACATCC

TCAAGGAGAA GCTGCTGGAC TATCACCTGC TCACTGACAA CTTCCCCTGC
```

-continued

```
CACTTTGTCT CTGCCTTTGG AGCCGGCTTC TGTGCCACAG TGGTGGCCTC

CCCGGTGGAC GTGGTGAAGA CCCGGTATAT GAACTCACCT CCAGGCCAGT

ACTTCAGCCC CCTCGACTGT ATGATAAAGA TGGTGGCCCA GGAGGGCCCC

ACAGCCTTCT ACAAGGGATT TACACCCTCC TTTTTGCGTT TGGGATCCTG

GAACGTGGTG ATGTTCGTAA CCTATGAGCA GCTGAAACGG GCCCTGATGA

AAGTCCAGAT GTTACGGGAA TCACCGTTTT GAACAAGACA AGAAGGCCAC

TGGTAGCTAA CGTGTCCGAA ACCAGTTAAG AATGGAAGAA AACGGTGCAT

CCACGCACAC ATGGACACAG ACCCACACAT GTTTACAGAA CTGTTGTTTA

CTTGTTGCTG ATTCAAGAAA CAGAAGTAGA AGAGAGAGGA TTCTGGTCTT

CACTGCCATG CCTCAAGAAC ACCTTTGTTT TGCACTGACA AGATGGAAAA

TAAATTATAT TAATTTTTGA AACCCATTAG GCATGCCTAA TATTTAGGCA

AGAGAAAATA AACCAAGATA GATCCATTTG GACAAAATGG AAGGTTGGAG

ACGTGTATCC CCGTGAAATC TGGTCAGATA ATGAATGATA AGCAGGAAGG

ATGGCAAGCA CGGGACAGGA GGGGCCCACA ATGGAGTGGG AGATCAGCCA

CGGAGCCTGG AGGGACGCCA CCCAGCAACA CAGAGCTGGC GACTGCAGCT

GCACCATCAC ACATGCATCA TCAGCCTATT TGTAATATGT CTGCCACAGA

GAGTCCTTTG GGATTCTAGG AAACCCAAGG AACAAGAGAA AAAACTAGAG

CCTGTGCTAA AGAAGCCTGC TGGGCCCATG TGAGGCTGGG GTCGTAAATA

TTCCCCGACG ACACTGAAGA ATCAAGAGGG CAGCCCCCAC TTCTCCTACA

AAATGGAGGG AGCCATCCCT TCCCTGTCCA CCTCACCAGG GGTGCTATGA

CATGCAAGTG AGAAGCTGGG CATGAACGCA CTTTATAAAA GCAAAAGCTC

TGTGTAAATC TAACTACAAG GACAATGCCT TGGGAGAGAT TTTGTCGGGA

CAGAGAGGAG TTGCCAGGGA AGAAGGTTTG AAAGATACGG TTGTCTAGAG

GTGAGACCAA AGGATCCAGA GACTTGGGGA CCAGAGGTGA CAGTGGATGA

CGTGAAGCCA CAGGAGCCCC ACCCCATGC AGCTTTTTCC CCACCCCCCC

CACCACGCGC TCAATCATGA GTACCTCAAA GGATTGTTGG GCTTGGGGGA

AAAGAGGTGG ATTCCTGGGC AAGAACCTAA AGTAGCAGGA,
``` as set forth in SEQ ID NO:11.

13. An expression vector for the expression of a human uncoupling protein 3 in a recombinant host cell wherein said expression vector comprises the DNA molecule of claim 12.

\* \* \* \* \*